United States Patent
Satou et al.

(10) Patent No.: US 9,902,798 B2
(45) Date of Patent: Feb. 27, 2018

(54) COMPOUND CONTAINING PHENOLIC HYDROXYL GROUP, PHENOLIC RESIN, CURABLE COMPOSITION, CURED PRODUCT THEREOF, SEMICONDUCTOR SEALING MATERIAL, AND PRINTED CIRCUIT BOARD

(71) Applicant: DIC Corporation, Tokyo (JP)

(72) Inventors: Yutaka Satou, Ichihara (JP); Ayumi Takahashi, Ichihara (JP); Gensuke Akimoto, Ichihara (JP)

(73) Assignee: DIC Corporation, Tokyo (JP)

( * ) Notice: Subject to any disclaimer, the term of this patent is extended or adjusted under 35 U.S.C. 154(b) by 165 days.

(21) Appl. No.: 14/897,915

(22) PCT Filed: Feb. 21, 2014

(86) PCT No.: PCT/JP2014/054139
§ 371 (c)(1),
(2) Date: Dec. 11, 2015

(87) PCT Pub. No.: WO2014/199661
PCT Pub. Date: Dec. 18, 2014

(65) Prior Publication Data
US 2016/0137771 A1 May 19, 2016

(30) Foreign Application Priority Data
Jun. 14, 2013 (JP) ................................ 2013-125566

(51) Int. Cl.
| | | |
|---|---|---|
| C08G 8/20 | (2006.01) |
| C08G 59/62 | (2006.01) |
| H01L 23/29 | (2006.01) |
| H05K 1/03 | (2006.01) |
| C07C 39/15 | (2006.01) |
| C08G 8/02 | (2006.01) |
| C08G 61/02 | (2006.01) |
| C08L 61/16 | (2006.01) |
| C08K 3/04 | (2006.01) |
| C08K 7/18 | (2006.01) |
| H05K 1/09 | (2006.01) |
| C09D 163/00 | (2006.01) |
| C08L 65/00 | (2006.01) |

(52) U.S. Cl.
CPC ............... *C08G 8/02* (2013.01); *C07C 39/15* (2013.01); *C08G 59/621* (2013.01); *C08G 61/02* (2013.01); *C08K 3/04* (2013.01); *C08K 7/18* (2013.01); *C08L 61/16* (2013.01); *C09D 163/00* (2013.01); *H01L 23/295* (2013.01); *H05K 1/0366* (2013.01); *H05K 1/09* (2013.01); *C08L 65/00* (2013.01); *H01L 2924/0002* (2013.01)

(58) Field of Classification Search
CPC .. H05K 1/0313; H05K 1/0353; H05K 1/0366; H05K 1/0373; C08G 8/02; C08G 8/20; C08G 59/621

USPC .................................................... 528/107, 125
See application file for complete search history.

(56) References Cited

FOREIGN PATENT DOCUMENTS

| JP | 41-012230 B | 7/1966 |
|---|---|---|
| JP | 04-360146 A | 12/1992 |
| JP | 06-049196 A | 2/1994 |
| JP | 2002-114889 A | 4/2002 |
| JP | 2013-023613 A | 2/2013 |
| JP | 5682805 B1 | 3/2015 |

OTHER PUBLICATIONS

Machine translation of JP 2013-023613A, Feb. 2013.*
Ke-Qing Ling et.al., "Copper(II)-Mediated Autoxidation of *tert*-Butylresorcinols," J. Org. Chem., 2003, 68(4), pp. 1358-1366.
(Continued)

*Primary Examiner* — Ramsey E Zacharia
(74) *Attorney, Agent, or Firm* — Locke Lord LLP; James E. Armstrong, IV; Nicholas J. DiCeglie, Jr.

(57) ABSTRACT

There are provided a compound containing a phenolic hydroxyl group, which exhibits excellent heat resistance and excellent flame retardancy in terms of a cured product thereof, a phenolic resin including the same, a curable composition and a cured product thereof, a semiconductor sealing material, and a printed circuit board. The phenolic resin contains a binuclear compound (X) represented by the following Structural Formula (I), and a trinuclear compound (Y) represented by the following Structural Formula (II) as essential components:

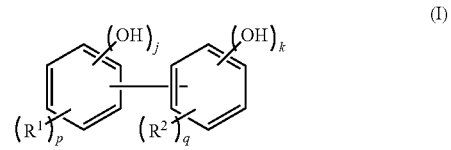

(I)

wherein each of j and k is 1 or 2, and at least one of j and k is 2;

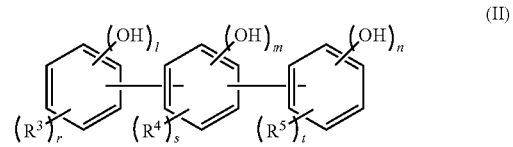

(II)

wherein each of l, m and n is 1 or 2, and at least one of l, m, and n is 2.

6 Claims, 4 Drawing Sheets

(56) References Cited

OTHER PUBLICATIONS

M. Victoria Gomez et.al., "Synergy between microwave irradiation and heterogeneous catalysis in an environmentally friendly self-condensation of hydroxybenzene derivatives," ARKIVOC, 2010, (iii), pp. 264-273.

International Search Report dated May 20, 2014, issued for PCT/JP2014/054139.

* cited by examiner

[Fig.1]
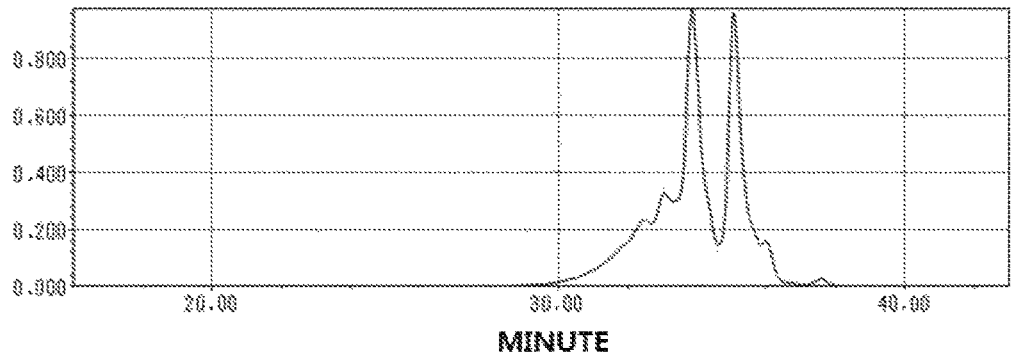
[Fig.2]
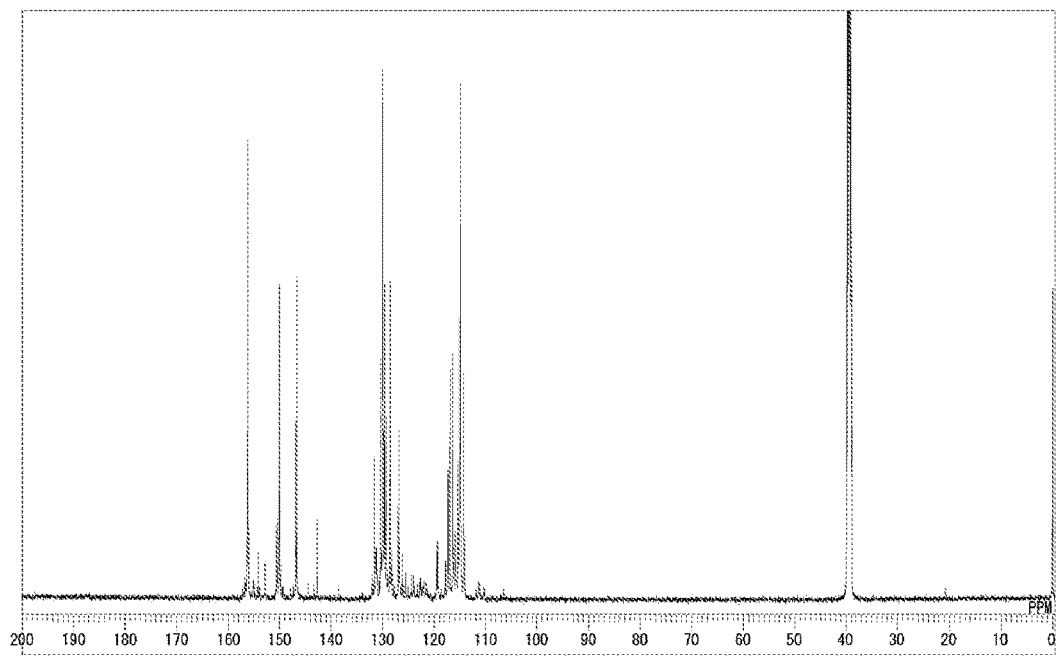

[Fig.3]
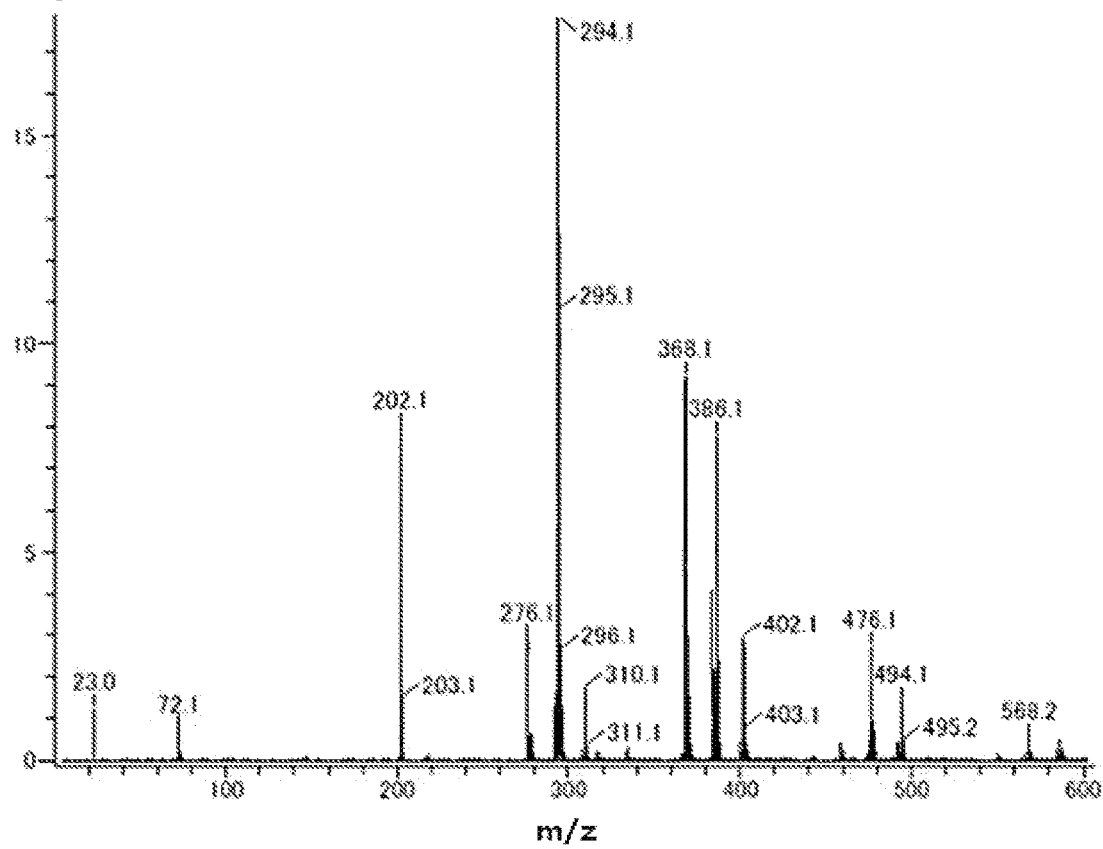
[Fig.4]
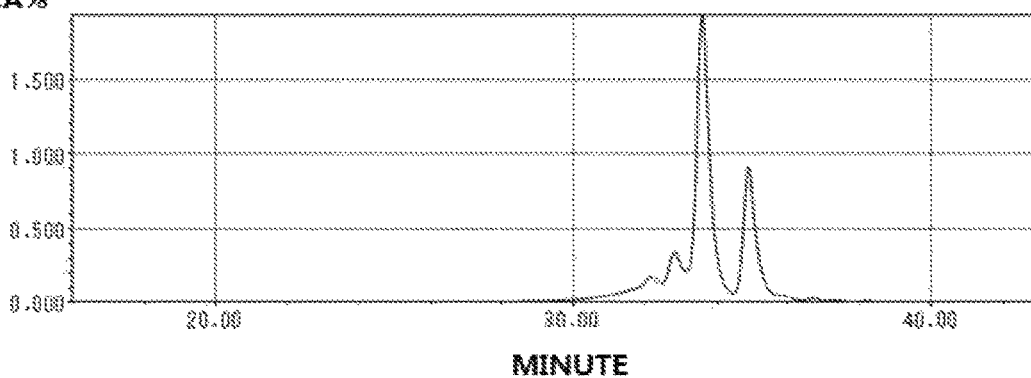

[Fig.5]
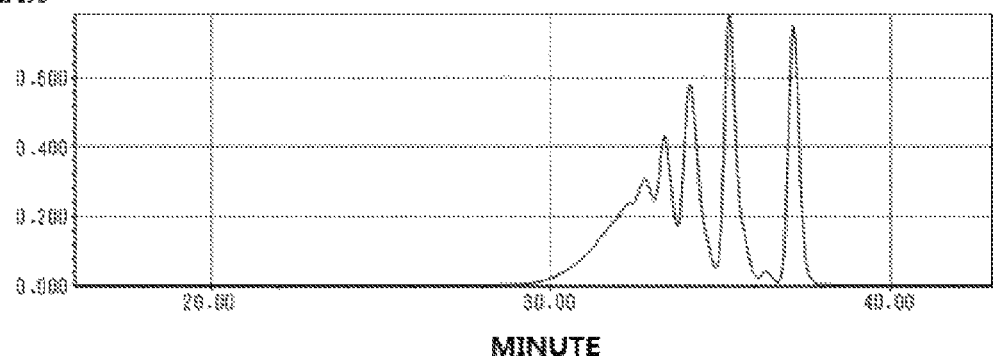
[Fig.6]
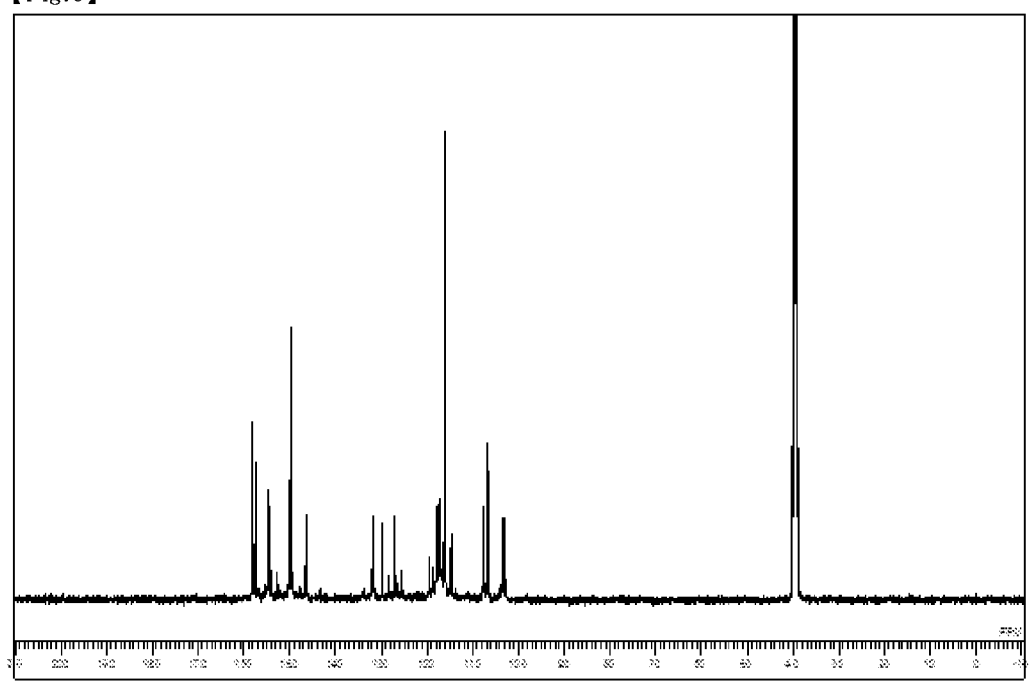

[Fig.7]
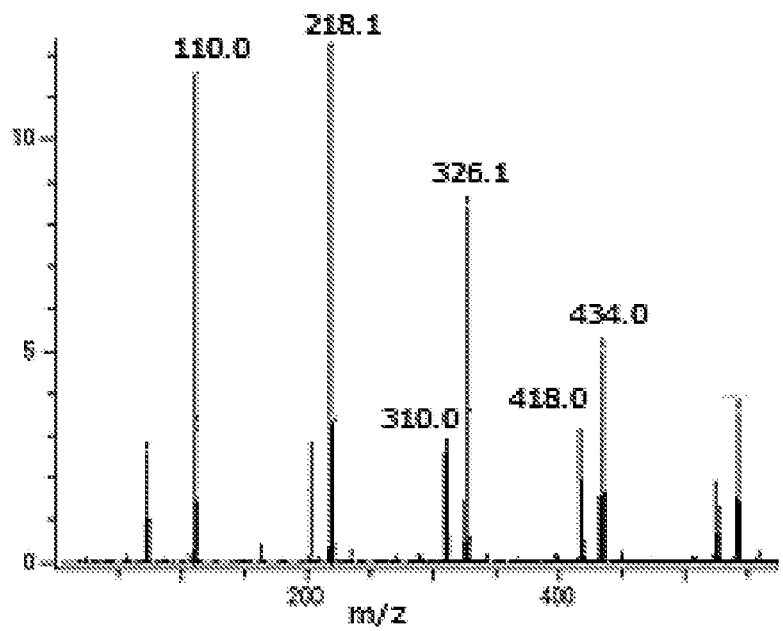
[Fig.8]
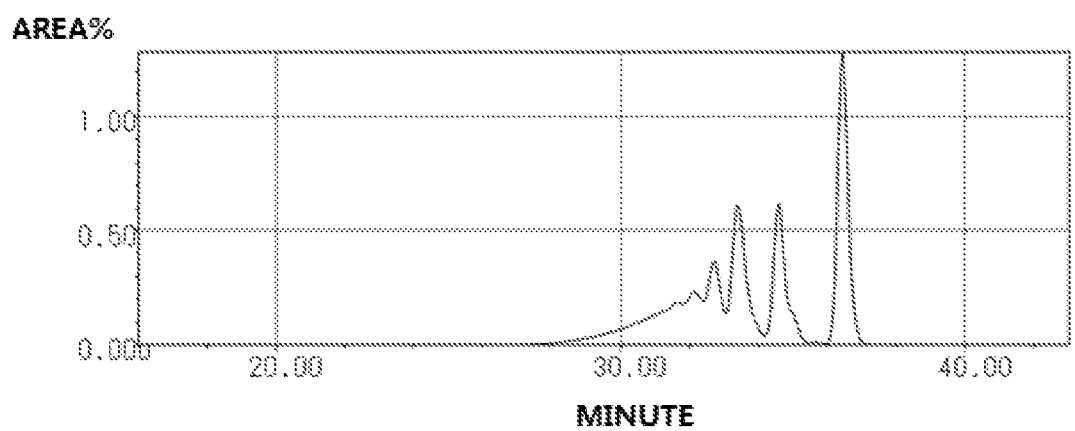

COMPOUND CONTAINING PHENOLIC HYDROXYL GROUP, PHENOLIC RESIN, CURABLE COMPOSITION, CURED PRODUCT THEREOF, SEMICONDUCTOR SEALING MATERIAL, AND PRINTED CIRCUIT BOARD

TECHNICAL FIELD

The present invention relates to a compound containing a phenolic hydroxyl group which exhibits excellent heat resistance and flame retardancy in terms of a cured product thereof, a phenolic resin including the same, a curable composition and a cured product thereof, a semiconductor sealing material, and a printed circuit board.

BACKGROUND ART

A phenolic resin has been used, for example, as a curing agent for epoxy resins, and an epoxy resin composition which is cured by a phenolic resin as a curing agent is widely used in electrical and electronic fields such as a semiconductor sealing material and a printed circuit board insulating material from the viewpoint that the cured product has excellent heat resistance and moisture resistance, in addition to an adhesive, a molding material, and a coating material.

Among these, a power semiconductor represented by a power module for an automobile is a technology crucial to energy saving in electrical and electronic equipment, and with a larger current, miniaturization, and high efficiency of a power semiconductor, transition from a silicon (Si) semiconductor in the related art to a silicon carbide (SiC) semiconductor has been advancing. The advantage of the SiC semiconductor is that the SiC semiconductor can be operated under higher temperature conditions, and therefore, a semiconductor sealing material is required to have higher heat resistance than those of semiconductor sealing materials in the related art. In addition, it is also important for the required performance of a semiconductor sealing resin to exhibit high flame retardancy without using a halogen-based flame retardant, and a resin material which has such performance has been required.

As the resin material to cope with these various required characteristics, for example, the compound containing a phenolic hydroxyl group represented by the following structural formula is known (refer to PTL 1).

[Chem. 1]

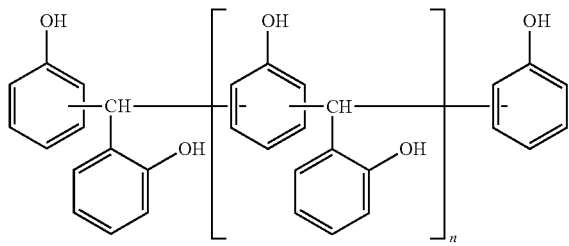

Such a compound containing a phenolic hydroxyl group exhibits extremely excellent heat resistance in terms of a cured product thereof; however, does not have sufficient flame retardancy.

CITATION LIST

Patent Literature

[PTL 1] JP-A-2002-114889

SUMMARY OF INVENTION

Technical Problem

Therefore, an object of the present invention is to provide a phenolic resin which exhibits excellent heat resistance and flame retardancy in terms of a cured product thereof, a curable composition and a cured product thereof, a semiconductor sealing material, and a printed circuit board.

Solution to Problem

As a result of thorough studies in order to achieve the above object, the present inventors found that a phenolic resin containing a binuclear compound having a specific structure and a trinuclear compound having a specific structure as essential components exhibits excellent heat resistance and flame retardancy in terms of a cured product thereof, and completed the present invention.

That is, the present invention relates to a phenolic resin containing a binuclear compound (X) represented by the following Structural Formula (I), and a trinuclear compound (Y) represented by the following Structural Formula (II) as essential components:

[Chem. 2]

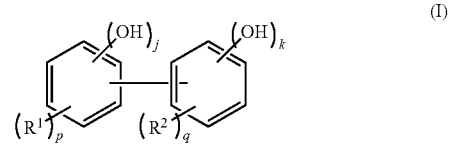

(I)

wherein each of $R^1$ and $R^2$ is any one of an alkyl group having 1 to 4 carbon atoms, an alkoxy group having 1 to 4 carbon atoms, an aryl group and an aralkyl group, each of p and q is 0, 1 or 2, in a case where p or q is 2, two $R^1$'s or $R^2$'s may be the same as or different from each other, each of j and k is 1 or 2, and at least one of j and k is 2;

[Chem. 3]

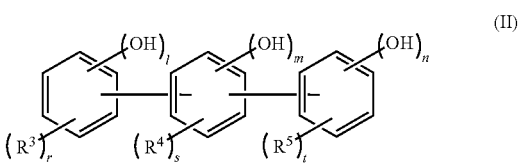

(II)

wherein each of $R^3$, $R^4$, and $R^5$ is any one of an alkyl group having 1 to 4 carbon atoms, an alkoxy group having 1 to 4 carbon atoms, an aryl group and an aralkyl group, each of r, s, and t is 0, 1 or 2, in a case where r, s, or t is 2, two $R^3$'s, $R^4$'s, or $R^5$'s may be the same as or different from each other, each of l, m and n is 1 or 2, and at least one of l, m and n is 2.

The present invention further relates to a curable composition including the phenolic resin and a curing agent, as essential components.

The present invention still further relates to a cured product which is obtained by a curing reaction of the curable composition.

The present invention still further relates to a semiconductor sealing material containing the curable composition and an inorganic filler.

The present invention still further relates to a printed circuit board obtained by impregnating a reinforcement basic material with a resin composition vanished by blending the curable composition with an organic solvent, and superposing a copper foil on the resulting material, followed by heat-pressing.

Advantageous Effects of Invention

According to the present invention, it is possible to provide a phenolic resin which exhibits excellent heat resistance and flame retardancy in terms of a cured product thereof, a curable composition and a cured product thereof, a semiconductor sealing material, and a printed circuit board.

BRIEF DESCRIPTION OF DRAWINGS

FIG. 1 is a GPC chart of a phenolic resin (1) obtained in Example 1.

FIG. 2 is a 13C-NMR chart of the phenolic resin (1) obtained in Example 1.

FIG. 3 is an MS spectrum of the phenolic resin (1) obtained in Example 1.

FIG. 4 is a GPC chart of a phenolic resin (2) obtained in Example 2.

FIG. 5 is a GPC chart of a phenolic resin (3) obtained in Example 3.

FIG. 6 is a 13C-NMR chart of the phenolic resin (3) obtained in Example 3.

FIG. 7 is an MS spectrum of the phenolic resin (3) obtained in Example 3.

FIG. 8 is a GPC chart of a phenolic resin (4) obtained in Example 4.

DESCRIPTION OF EMBODIMENTS

Hereinafter, the present invention will be described in detail.

The phenolic resin of the present invention contains a binuclear compound (X) represented by the following Structural Formula (I) and a trinuclear compound (Y) represented by the following Structural Formula (II) as essential components:

[Chem. 4]

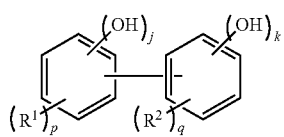
(I)

wherein each of $R^1$ and $R^2$ is any one of an alkyl group having 1 to 4 carbon atoms, an alkoxy group having 1 to 4 carbon atoms, an aryl group and an aralkyl group, each of p and q is 0, 1 or 2, in a case where p or q is 2, two $R^1$'s or $R^2$'s may be the same as or different from each other, each of j and k is 1 or 2, and at least one of j and k is 2;

[Chem. 5]

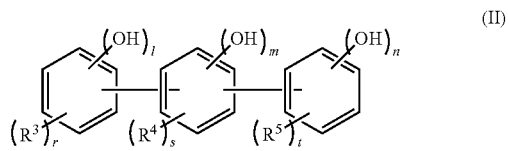
(II)

wherein each of $R^3$, $R^4$, and $R^5$ is any one of an alkyl group having 1 to 4 carbon atoms, an alkoxy group having 1 to 4 carbon atoms, an aryl group and an aralkyl group, each of r, s, and t is 0, 1 or 2, in a case where r, s or t is 2, two $R^3$'s, $R^4$'s or $R^5$'s may be the same as or different from each other, each of 1, m and n is 1 or 2, and at least one of 1, m and n is 2.

The compound containing a phenolic hydroxyl group has a low molecular weight, and a high aromatic ring concentration and a high hydroxyl group concentration since the compound containing a phenolic hydroxyl group has a structure in which aromatic nuclei are mutually boned not through a methylene chain. Such a compound tends to be decreased in flame retardancy since the concentration of a hydroxyl group exhibiting flammability is increased and a large number of reactive groups exist in close proximity, while it exhibits excellent heat resistance in terms of a cured product thereof. In contrast, the compound containing a phenolic hydroxyl group of the present invention exhibits both excellent heat resistance and flame retardancy in terms of a cured product thereof since the compound has a biphenyl skeleton or a terphenyl skeleton and the hydroxyl group in the molecule has excellent reactivity.

As the contents of the binuclear compound (X) and the trinuclear compound (Y) in the phenolic resin of the present invention, it is more preferable that the content of the binuclear compound (X) is within a range of 2% to 50% in area ratio in a GPC measurement, and the content of the trinuclear compound (Y) is within a range of 10% to 95% in area ratio in a GPC measurement, since the melt viscosity, and the balance between heat resistance and flame retardancy of the cured product are more excellent.

Moreover, in the present invention, the content of the binuclear compound (X), the trinuclear compound (Y), or other components in the phenolic resin refers to a proportion of the peak area of each component with respect to the total peak area of the phenolic resin, which is calculated from GPC measurement data under the following conditions.

<GPC Measurement Conditions>

Measurement apparatus: "HLC-8220 GPC" manufactured by Tosoh Corporation

Column: guard column "HXL-L" manufactured by Tosoh Corporation+"TSK-GEL G2000HXL" manufactured by Tosoh Corporation+"TSK-GEL G2000HXL" manufactured by Tosoh Corporation+"TSK-GEL G3000HXL" manufactured by Tosoh Corporation+"TSK-GEL G4000HXL" manufactured by Tosoh Corporation Detector: RI (differential refractometer)

Data processing: "GPC-8020 model II Version 4.10" manufactured by Tosoh Corporation Measurement Conditions:

| | |
|---|---|
| column temperature | 40° C. |
| eluent | tetrahydrofuran |
| flow rate | 1.0 ml/min |

Standard: according to the measurement manual of the "GPC-8020 model II Version 4.10", the following monodisperse polystyrene of which the molecular weight is known is used.

(Polystyrene Used)
"A-500" manufactured by Tosoh Corporation
"A-1000" manufactured by Tosoh Corporation
"A-2500" manufactured by Tosoh Corporation
"A-5000" manufactured by Tosoh Corporation
"F-1" manufactured by Tosoh Corporation
"F-2" manufactured by Tosoh Corporation
"F-4" manufactured by Tosoh Corporation
"F-10" manufactured by Tosoh Corporation
"F-20" manufactured by Tosoh Corporation
"F-40" manufactured by Tosoh Corporation
"F-80" manufactured by Tosoh Corporation
"F-128" manufactured by Tosoh Corporation Sample: a solution (50 µl) obtained by filtering a tetrahydrofuran solution of 1.0% by mass in terms of the resin solid content through a microfilter.

As the phenolic resin of the present invention, a resin prepared by a method in which a compound (Q) having a quinone structure in the molecular structure and a compound (P) having a phenolic hydroxyl group in the molecular structure are reacted with each other at a temperature range of 40° C. to 180° C. under non-catalytic or acid catalytic conditions is exemplified.

As the compound (Q) having a quinone structure in the molecular structure, for example, the compound represented by the following Structural Formula (Q1) is exemplified.

[Chem. 6]

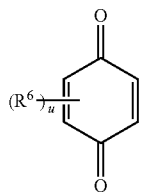

(Q1)

In the formula, $R^6$ is any one of an alkyl group having 1 to 4 carbon atoms, an alkoxy group having 1 to 4 carbon atoms, an aryl group and an aralkyl group, u is 0, 1 or 2, and in a case where u is 2, two $R^6$'s may be the same as or different from each other, and specific examples thereof include parabenzoquinone and 2-methyl benzoquinone. These may be used alone respectively, or two or more types may be used in combination.

As the compound (P) having a phenolic hydroxyl group in the molecular structure, for example, the compound represented by the following Structural Formula (P1) is exemplified.

[Chem. 7]

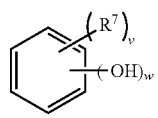

(P1)

In the formula, $R^7$ is any one of an alkyl group having 1 to 4 carbon atoms, an alkoxy group having 1 to 4 carbon atoms, an aryl group and an aralkyl group, v is 0, 1 or 2, in a case where v is 2, two $R^7$'s may be the same as or different from each other, and w is 1 or 2, and specific examples thereof include phenol, ortho-cresol, meta-cresol, para-cresol, 2,6-dimethylphenol, 2,5-dimethylphenol, 2,4-dimethylphenol, 3,5-dimethylphenol, 4-isopropylphenol, 4-tert-butylphenol, 2-methoxyphenol, 3-methoxyphenol, 4-methoxyphenol, 2-methoxy-4-methylphenol, 2-tert-butyl-4-methoxyphenol, 2,6-dimethoxyphenol, 3,5-dimethoxyphenol, 2-ethoxyphenol, 3-ethoxyphenol, 4-ethoxyphenol, 2-phenylphenol, 3-phenylphenol, 4-phenylphenol, 4-benzylphenol, 1,2-dihydroxybenzene, 1,3-dihydroxybenzene, and 1,4-dihydroxybenzene. These may be used alone respectively, or two or more types may be used in combination.

Among these, phenol or various types of dihydroxybenzene are more preferable since a phenolic resin which exhibits excellent heat resistance and flame retardancy in terms of a cured product thereof is obtained.

Since the reactivity of the reaction of the compound (Q) having a quinone structure in the molecular structure with the compound (P) having a phenolic hydroxyl group in the molecular structure is high, the reaction proceeds even under non-catalytic conditions; however, the reaction may be performed by using a suitable acid catalyst. Examples of the acid catalyst used here include inorganic acids such as hydrochloric acid, sulfuric acid, and phosphoric acid, organic acids such as methanesulfonic acid, p-toluenesulfonic acid, and oxalic acid, or Lewis acids such as boron trifluoride, anhydrous aluminum chloride, and zinc chloride. In the case of using one of the acid catalysts described above, the acid catalyst is preferably used in the amount of 5.0% by mass or less with respect to the total mass of the compound (Q) having a quinone structure in the molecular structure and the compound (P) having a phenolic hydroxyl group in the molecular structure.

In addition, the reaction is preferably performed under solvent-free conditions; however, the reaction may be performed in an organic solvent, as necessary. Examples of the organic solvent used here include methyl cellosolve, isopropyl alcohol, ethyl cellosolve, toluene, xylene, and methyl isobutyl ketone. In the case of using one of the organic solvents described above, the organic solvent is preferably used in a proportion within a range of 50 parts by mass to 200 parts by mass with respect to the total 100 parts by mass of the compound (Q) having a quinone structure in the molecular structure and the compound (P) having a phenolic hydroxyl group in the molecular structure, from the viewpoint of improvement of reaction efficiency.

After the reaction of the compound (Q) having a quinone structure in the molecular structure with the compound (P) having a phenolic hydroxyl group in the molecular structure ends, drying under reduced pressure is performed, whereby a desired phenolic resin can be obtained.

The phenolic resin of the present invention exhibits the effects of the present invention in which heat resistance and flame retardancy of the cured product are excellent as long as the phenolic resin contains the binuclear compound (X) represented by Structural Formula (I) and the trinuclear compound (Y) represented by Structural Formula (II) as essential components. Hereinafter, a more preferable phenolic resin of the present invention will be described in detail.

A phenolic resin (hereinafter, abbreviated as "phenolic resin (1)") obtained by using parabenzoquinone as the compound (Q) having a quinone structure in the molecular structure and phenol as the compound (P) having a phenolic hydroxyl group in the molecular structure exhibits excellent heat resistance and flame retardancy in terms of a cured product thereof, among the phenolic resins of the present invention.

As the binuclear compound (X) represented by Structural Formula (I) contained in the phenolic resin (1), a compound represented by any one of the following Structural Formulas (1-1) and (1-2) is exemplified.

[Chem. 8]

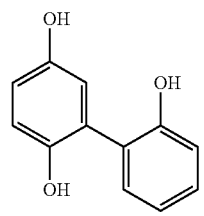
(1-1)

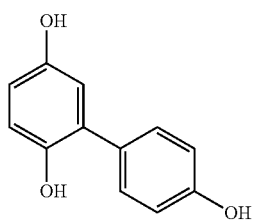
(1-2)

As the trinuclear compound (Y) represented by Structural Formula (II) contained in the phenolic resin (1), a compound represented by any one of the following Structural Formulas (1-3) to (1-6) is exemplified.

[Chem. 9]

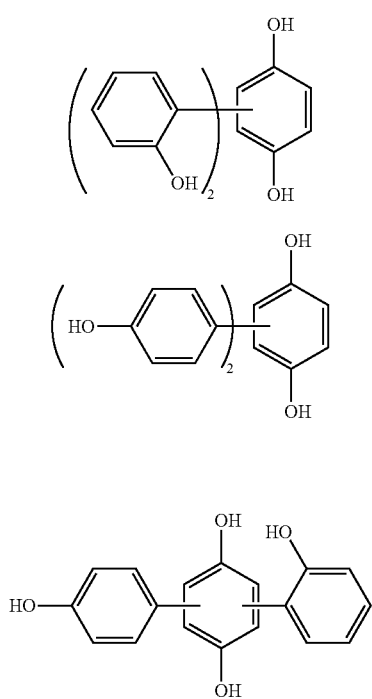

(1-3)

(1-4)

(1-5)

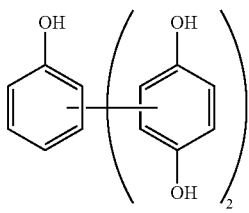
(1-6)

As described above, the phenolic resin of the present invention contains the binuclear compound (X) and the trinuclear compound (Y) as essential components. As the content of each component in the phenolic resin (1), it is preferable that the content of the binuclear compound (X) is within a range of 2% to 50% in area ratio in a GPC measurement and the content of the trinuclear compound (Y) is within a range of 10% to 95% in area ratio in a GPC measurement, and it is more preferable that the content of the binuclear compound (X) is within a range of 10% to 50% in area ratio in a GPC measurement, and the content of the trinuclear compound (Y) is within a range of 10% to 50% in area ratio in a GPC measurement, since the melt viscosity is low, and heat resistance and flame retardancy of the cured product are more excellent.

Furthermore, from the viewpoint of obtaining a cured product having more excellent heat resistance, the phenolic resin (1) preferably contains a tetranuclear compound (Z) represented by any one of the following Structural Formulas (III-1) and (III-2), in addition to the binuclear compound (X) and the trinuclear compound (Y), and, at this time, the content of the tetranuclear compound (Z) in the phenolic resin (1) is preferably within a range of 2% to 30% in area ratio in a GPC measurement.

[Chem. 10]

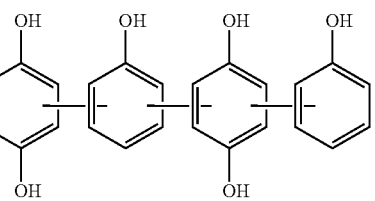
(III-1)

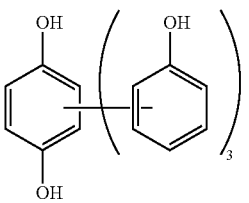
(III-2)

As the tetranuclear compound (Z) represented by Structural Formula (III-2), a compound represented by any one of the following Structural Formulas (1-7) to (1-10) is exemplified.

[Chem. 11]

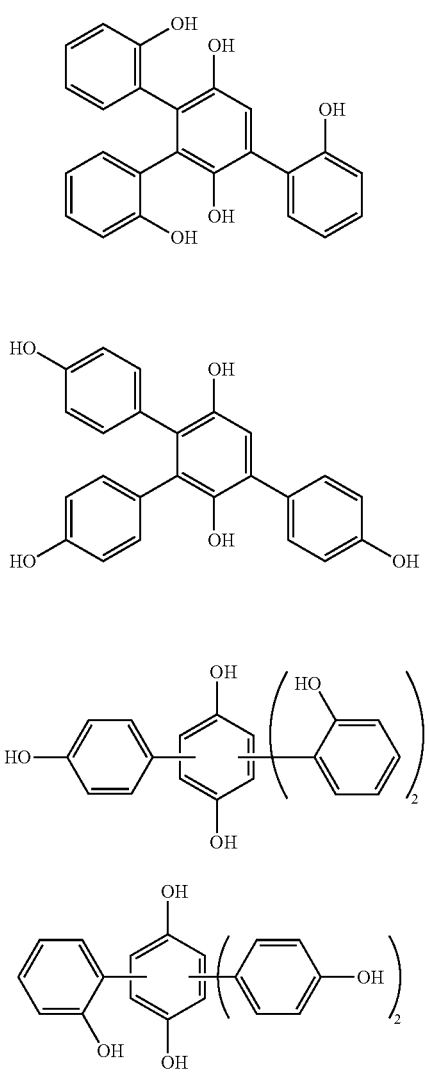

(1-7)

(1-8)

(1-9)

(1-10)

[Chem. 12]

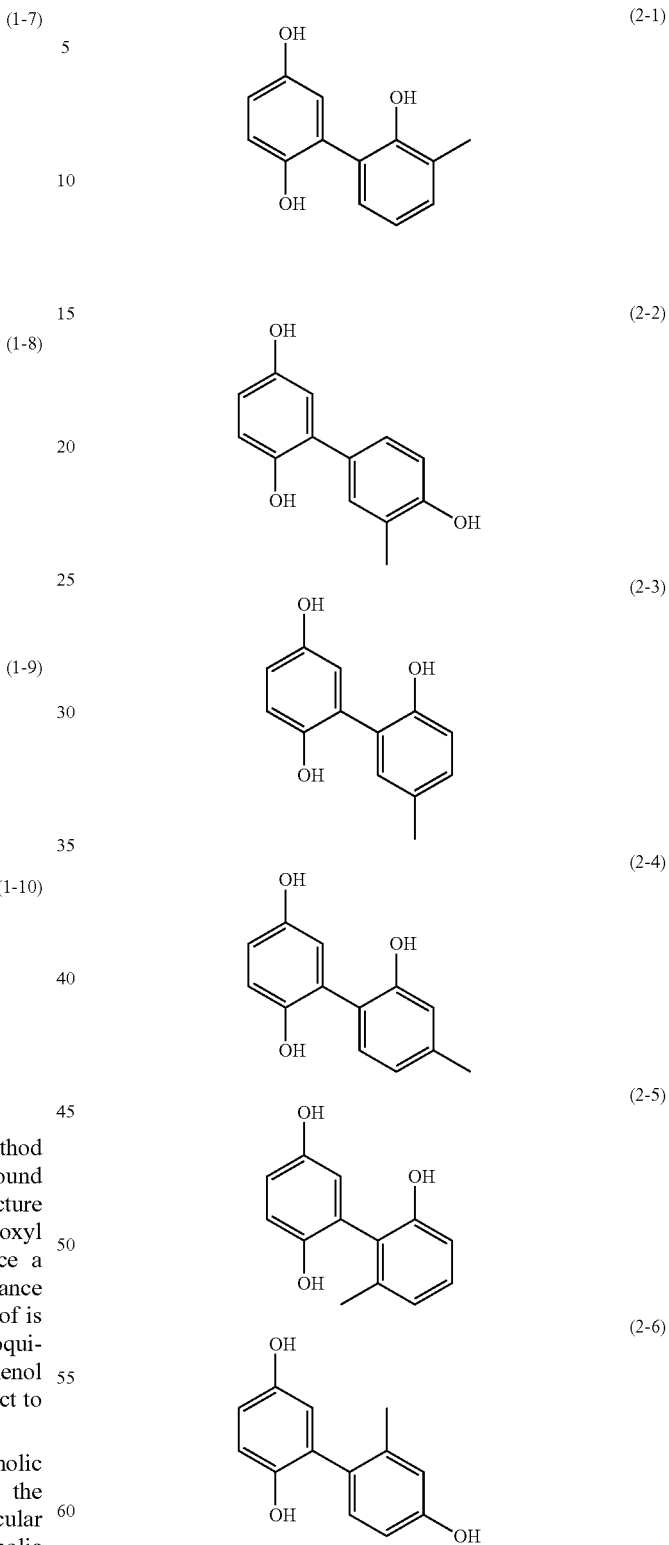

(2-1)

(2-2)

(2-3)

(2-4)

(2-5)

(2-6)

The phenolic resin (1) can be prepared by the method described above using parabenzoquinone as the compound (Q) having a quinone structure in the molecular structure and phenol as the compound (P) having a phenolic hydroxyl group in the molecular structure. At this time, since a phenolic resin which exhibits more excellent heat resistance and flame retardancy in terms of a cured product thereof is obtained, the reaction proportion between parabenzoquinone and phenol is preferably a proportion in which phenol is within a range of 0.1 moles to 10.0 moles with respect to 1 mole of parabenzoquinone.

A phenolic resin (hereinafter, abbreviated as "phenolic resin (2)") obtained by using parabenzoquinone as the compound (Q) having a quinone structure in the molecular structure and cresol as the compound (P) having a phenolic hydroxyl group in the molecular structure will be described.

As the binuclear compound (X) represented by Structural Formula (I) contained in the phenolic resin (2), a compound represented by any one of the following Structural Formulas (2-1) to (2-6) is exemplified.

As the trinuclear compound (Y) represented by Structural Formula (II) contained in the phenolic resin (2), a compound represented by any one of the following Structural Formulas (2-7) to (2-16) is exemplified.

[Chem. 13]

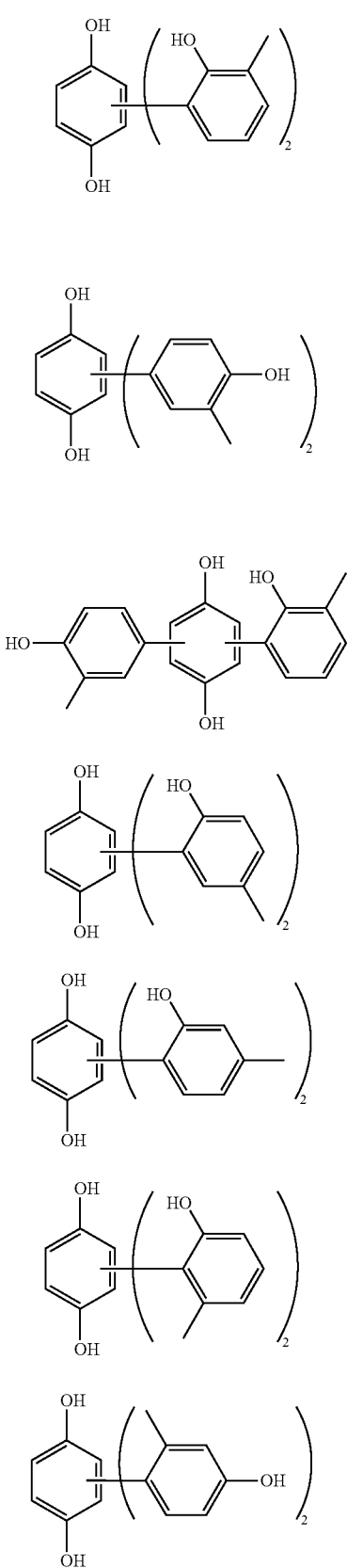

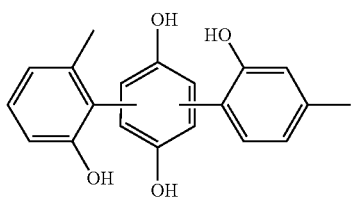

As described above, the phenolic resin of the present invention contains the binuclear compound (X) and the trinuclear compound (Y) as essential components. As the content of each component in the phenolic resin (2), it is preferable that the content of the binuclear compound (X) is within a range of 2% to 50% in area ratio in a GPC measurement and the content of the trinuclear compound (Y) is within a range of 10% to 95% in area ratio in a GPC measurement, and it is more preferable that the content of the binuclear compound (X) is within a range of 10% to 50% in area ratio in a GPC measurement, and the content of the trinuclear compound (Y) is within a range of 30% to 90% in area ratio in a GPC measurement, since heat resistance and flame retardancy of the cured product are excellent.

Furthermore, from the viewpoint of obtaining a cured product having more excellent heat resistance, the phenolic resin (2) preferably contains a tetranuclear compound (Z) represented by any one of the following Structural Formulas (III-3) and (III-4), in addition to the binuclear compound (X) and the trinuclear compound (Y), and, at this time, the content of the tetranuclear compound (Z) in the phenolic resin (2) is preferably within a range of 2% to 20% in area ratio in a GPC measurement.

[Chem. 14]

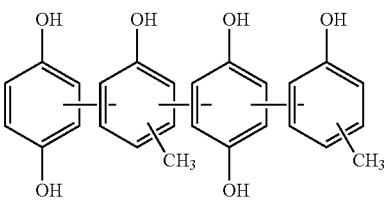

(III-4)
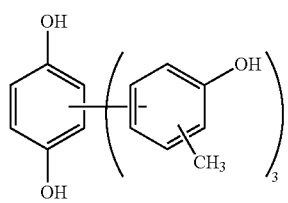
As the tetranuclear compound (Z) represented by Structural Formula (III-3) or (III-4), a compound represented by any one of the following Structural Formulas (2-17) to (2-34) is exemplified.
[Chem. 15]
(2-17)
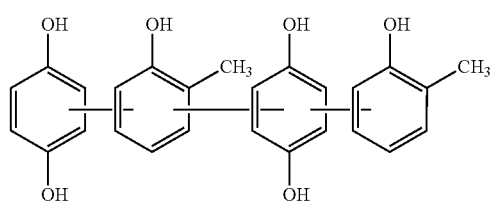
(2-18)
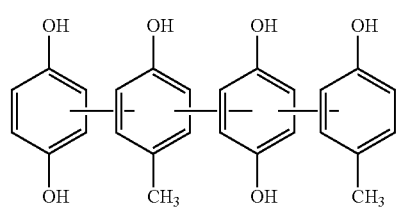
(2-19)
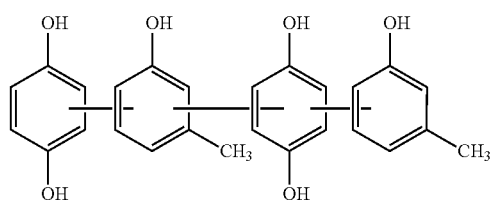
[Chem. 16]
(2-20)
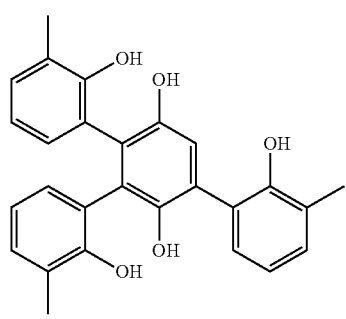
(2-21)
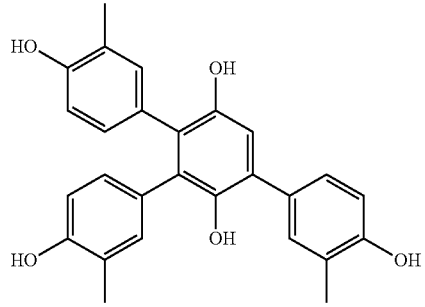
(2-22)
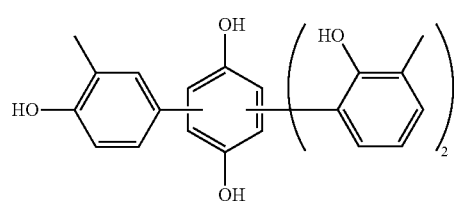
(2-23)
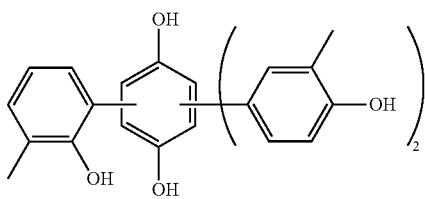
[Chem. 17]
(2-24)
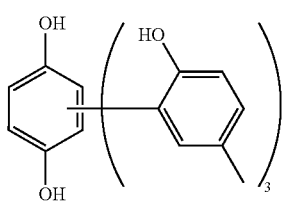
[Chem. 18]
(2-25)
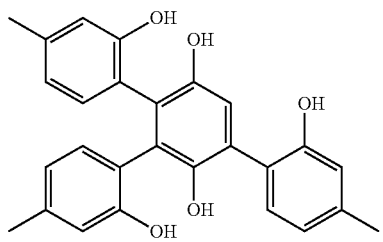
(2-26)
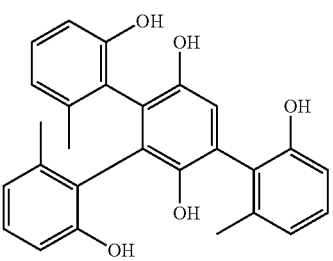

(2-27)
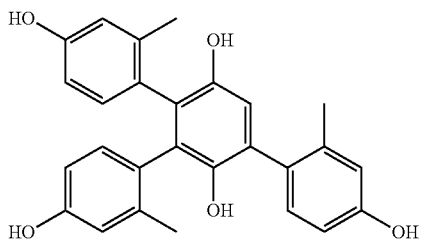

(2-28)
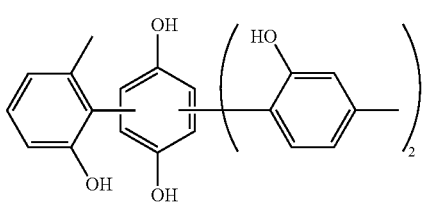

(2-29)
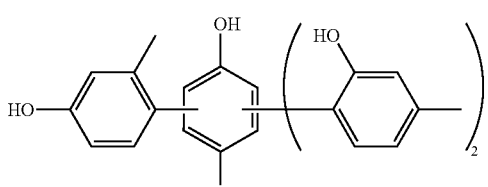

(2-30)
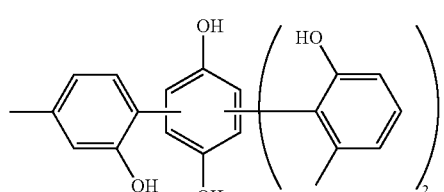

(2-31)
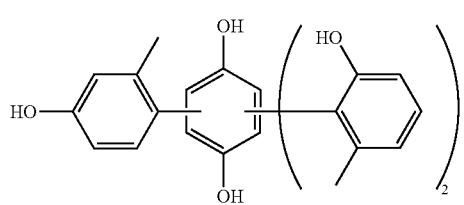

(2-32)
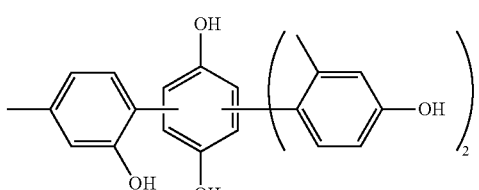

(2-33)
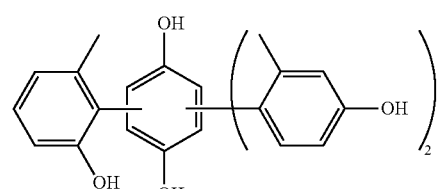

(2-34)
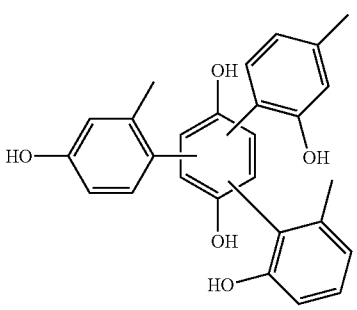

The phenolic resin (2) can be prepared by the method described above using parabenzoquinone as the compound (Q) having a quinone structure in the molecular structure and cresol as the compound (P) having a phenolic hydroxyl group in the molecular structure. At this time, since a phenolic resin which exhibits more excellent heat resistance and flame retardancy in terms of a cured product thereof is obtained, the reaction proportion between parabenzoquinone and cresol is preferably a proportion in which cresol is within a range of 0.1 moles to 10.0 moles with respect to 1 mole of parabenzoquinone.

The cresol used here may be any one of ortho-cresol, meta-cresol, and para-cresol, and plural types thereof may be used in combination. Among these, ortho-cresol is preferable since a phenolic resin which exhibits excellent heat resistance and flame retardancy in terms of a cured product thereof is obtained.

A phenolic resin (hereinafter, abbreviated as "phenolic resin (3)") obtained by using parabenzoquinone as the compound (Q) having a quinone structure in the molecular structure and dimethylphenol as the compound (P) having a phenolic hydroxyl group in the molecular structure will be described.

As the binuclear compound (X) represented by Structural Formula (I) contained in the phenolic resin (3), a compound represented by the following Structural Formula (3-1) is exemplified.

[Chem. 19]

(3-1)
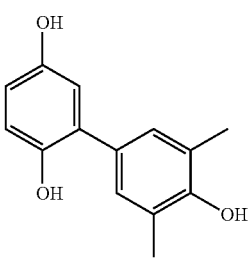

As the trinuclear compound (Y) represented by Structural Formula (II) contained in the phenolic resin (3), a compound represented by the following Structural Formula (3-2) is exemplified.

[Chem. 20]

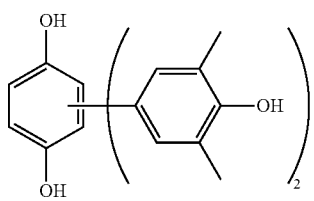
(3-2)

As described above, the phenolic resin of the present invention contains the binuclear compound (X) and the trinuclear compound (Y) as essential components. As the content of each component in the phenolic resin (3), it is preferable that the content of the binuclear compound (X) is within a range of 2% to 50% in area ratio in a GPC measurement and the content of the trinuclear compound (Y) is within a range of 10% to 95% in area ratio in a GPC measurement, and it is more preferable that the content of the binuclear compound (X) is within a range of 2% to 25% in area ratio in a GPC measurement, and the content of the trinuclear compound (Y) is within a range of 50% to 95% in area ratio in a GPC measurement, since the melt viscosity is low, and heat resistance and flame retardancy of the cured product are excellent.

Furthermore, from the viewpoint of obtaining a cured product having more excellent heat resistance, the phenolic resin (3) preferably contains a tetranuclear compound (Z) represented by any one of the following Structural Formulas (III-5) and (III-6) in addition to the binuclear compound (X) and the trinuclear compound (Y), and, at this time, the content of the tetranuclear compound (Z) in the phenolic resin (1) is preferably within a range of 0.5% to 10% in area ratio in a GPC measurement.

[Chem. 21]

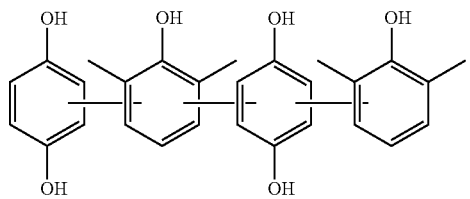
(III-5)

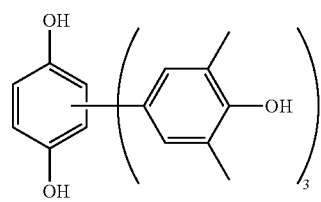
(III-6)

The phenolic resin (3) can be prepared by the method described above using parabenzoquinone as the compound (Q) having a quinone structure in the molecular structure and dimethylphenol as the compound (P) having a phenolic hydroxyl group in the molecular structure. At this time, since a phenolic resin which has low melt viscosity and exhibits more excellent heat resistance and flame retardancy in terms of a cured product thereof is obtained, the reaction proportion between parabenzoquinone and dimethylphenol is preferably a proportion in which dimethylphenol is within a range of 0.1 moles to 10.0 moles with respect to 1 mole of parabenzoquinone.

The dimethylphenol used here may be any regioisomer of 2,6-dimethylphenol, 2,5-dimethylphenol, 2,4-dimethylphenol, and 3,5-dimethylphenol. Among these, 2,6-dimethylphenol is preferable since a phenolic resin which exhibits excellent heat resistance and flame retardancy in terms of a cured product thereof is obtained.

A phenolic resin (hereinafter, abbreviated as "phenolic resin (4)") obtained by using parabenzoquinone as the compound (Q) having a quinone structure in the molecular structure and dihydroxybenzene as the compound (P) having a phenolic hydroxyl group in the molecular structure exhibits, in particular, excellent balance between heat resistance and flame retardancy in terms of a cured product thereof, among the phenolic resins of the present invention.

As the binuclear compound (X) represented by Structural Formula (I) contained in the phenolic resin (4), a compound represented by the following Structural Formula (4-1) or (4-2) is exemplified.

[Chem. 22]

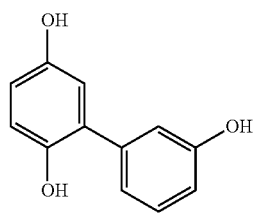
(4-1)

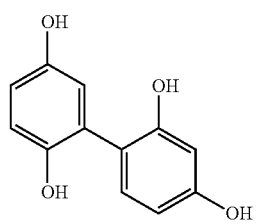
(4-2)

As the trinuclear compound (Y) represented by Structural Formula (II) contained in the phenolic resin (4), a compound represented by any one of the following Structural Formulas (4-3) to (4-6) is exemplified.

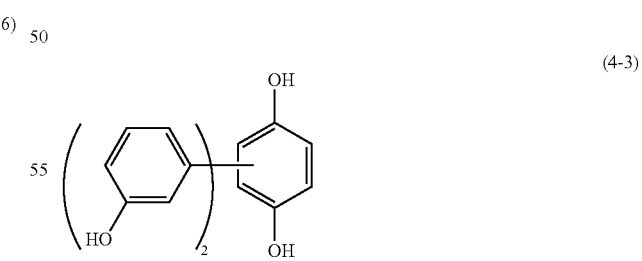
(4-3)

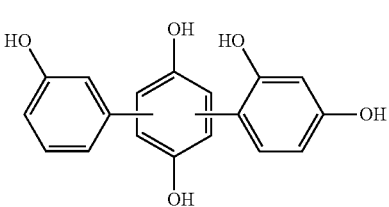
(4-4)

(4-5)

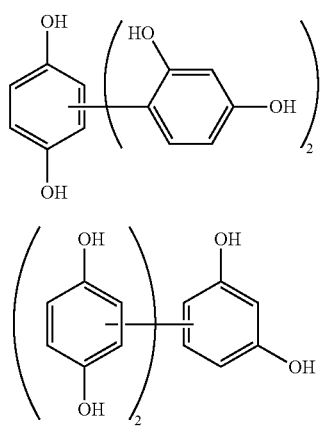

(4-6)

As the tetranuclear compound (Z) represented by Structural Formula (III-7) or (III-8), a compound represented by any one of the following Structural Formulas (4-7) to (4-19) is exemplified.

[Chem. 24]

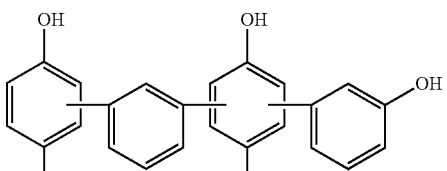
(4-7)

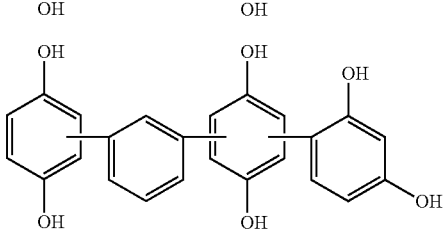
(4-8)

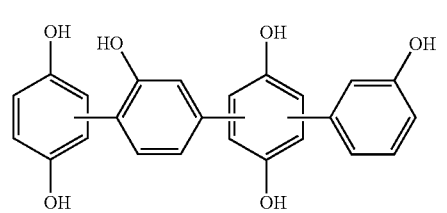
(4-9)

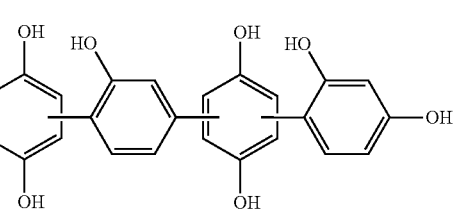
(4-10)

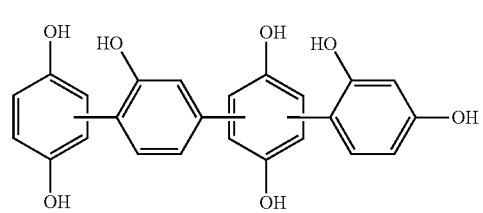
(4-11)

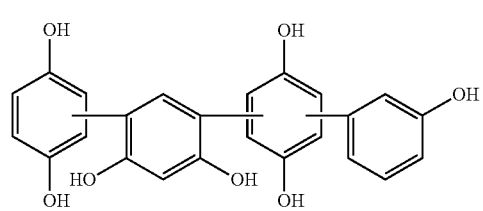
(4-12)

As described above, the phenolic resin of the present invention contains the binuclear compound (X) and the trinuclear compound (Y) as essential components. As the content of each component in the phenolic resin (4), it is preferable that the content of the binuclear compound (X) is within a range of 2% to 50% in area ratio in a GPC measurement and the content of the trinuclear compound (Y) is within a range of 10% to 95% in area ratio in a GPC measurement, and it is more preferable that the content of the binuclear compound (X) is within a range of 5% to 40% in area ratio in a GPC measurement, and the content of the trinuclear compound (Y) is within a range of 10% to 50% in area ratio in a GPC measurement, since heat resistance and flame retardancy of the cured product are excellent.

Furthermore, from the viewpoint of obtaining a cured product having more excellent heat resistance, the phenolic resin (4) preferably contains a tetranuclear compound (Z) represented by any one of the following Structural Formulas (III-7) and (III-8).

[Chem. 23]

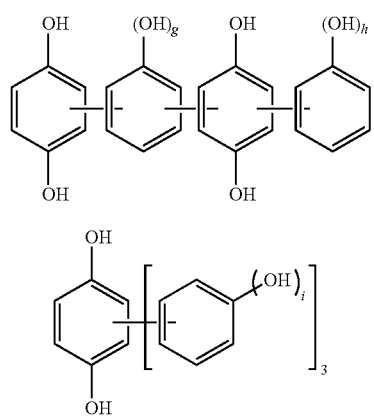

(III-7)

(III-8)

In the formula, g represents an integer of 0 to 2, h represents 1 or 2, and i represents 1 or 2, in addition to the binuclear compound (X) and the trinuclear compound (Y), and, at this time, the content of the tetranuclear compound (Z) in the phenolic resin (4) is preferably within a range of 5% to 40% in area ratio in a GPC measurement.

[Chem. 25]

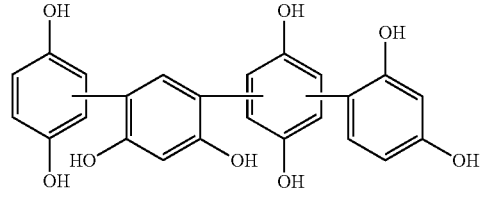
(4-13)

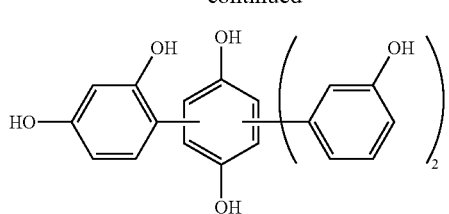
(4-14)

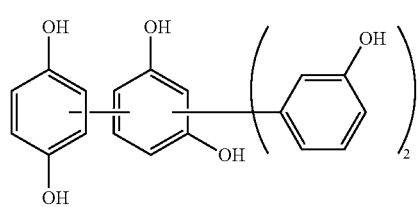
(4-15)

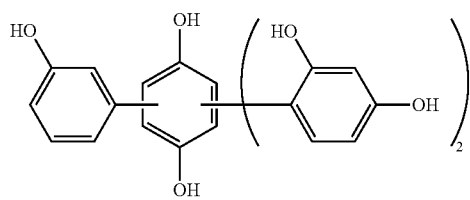
(4-16)

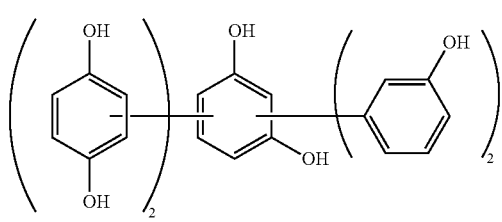
(4-17)

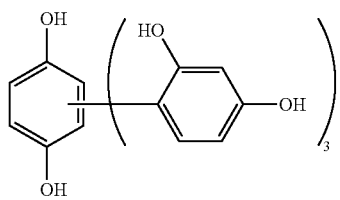
(4-18)

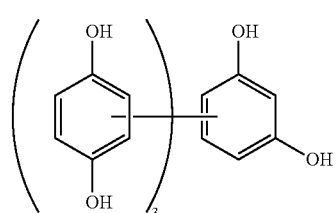
(4-19)

The phenolic resin (4) can be prepared by the method described above, for example, using parabenzoquinone as the compound (Q) having a quinone structure in the molecular structure and dihydroxybenzene as the compound (P) having a phenolic hydroxyl group in the molecular structure. At this time, since a phenolic resin which exhibits more excellent heat resistance and flame retardancy in terms of a cured product thereof is obtained, the reaction proportion between parabenzoquinone and dihydroxybenzene is preferably a proportion in which dihydroxybenzene is within a range of 0.1 moles to 10.0 moles with respect to 1 mole of parabenzoquinone.

The dihydroxybenzene used here may be any one of 1,2-dihydroxybenzene, 1,3-dihydroxybenzene, and 1,4-dihydroxybenzene. Among these, 1,3-dihydroxybenzene is preferable since a phenolic resin which exhibits excellent heat resistance and flame retardancy in terms of a cured product thereof is obtained.

A phenolic resin (hereinafter, abbreviated as "phenolic resin (5)") obtained by using parabenzoquinone as the compound (Q) having a quinone structure in the molecular structure and phenylphenol as the compound (P) having a phenolic hydroxyl group in the molecular structure will be described.

As the binuclear compound (X) represented by Structural Formula (I) contained in the phenolic resin (5), a compound represented by any one of the following Structural Formulas (5-1) to (5-3) is exemplified.

[Chem. 26]

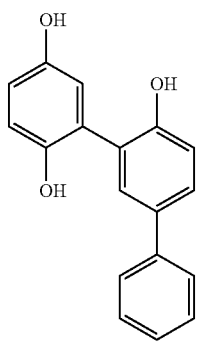
(5-1)

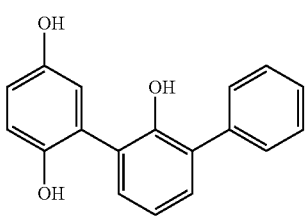
(5-2)

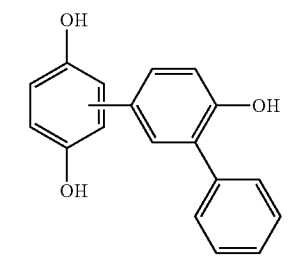
(5-3)

As the trinuclear compound (Y) represented by Structural Formula (II) contained in the phenolic resin (5), a compound represented by any one of the following Structural Formulas (5-4) to (5-7) is exemplified.

[Chem. 27]

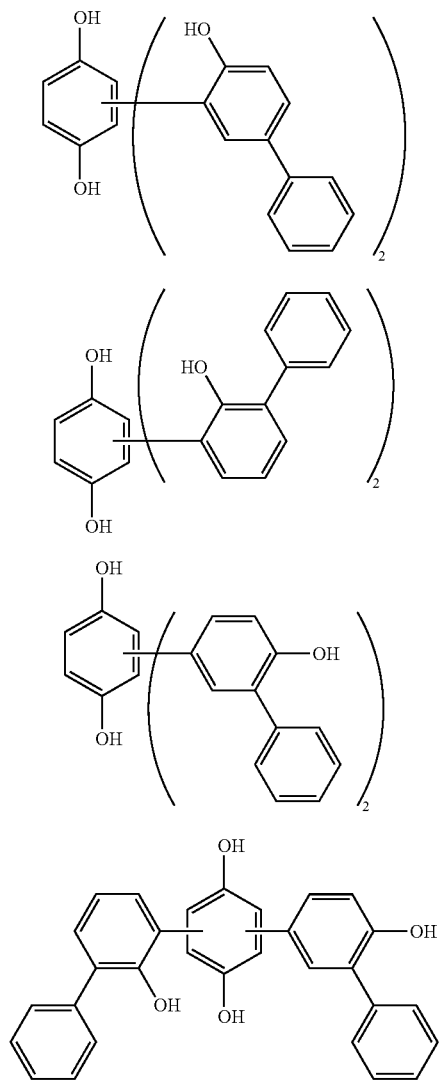

As described above, the phenolic resin of the present invention contains the binuclear compound (X) and the trinuclear compound (Y) as essential components. As the content of each component in the phenolic resin (5), it is preferable that the content of the binuclear compound (X) is within a range of 2% to 50% in area ratio in a GPC measurement, and the content of the trinuclear compound (Y) is within a range of 10% to 95% in area ratio in a GPC measurement, since the melt viscosity is low, and heat resistance and flame retardancy of the cured product are excellent.

The phenolic resin (5) can be prepared by the method described above using parabenzoquinone as the compound (Q) having a quinone structure in the molecular structure and phenylphenol as the compound (P) having a phenolic hydroxyl group in the molecular structure. At this time, since a phenolic resin which has low melt viscosity and exhibits more excellent heat resistance and flame retardancy in terms of a cured product thereof is obtained, the reaction proportion between parabenzoquinone and phenylphenol is preferably a proportion in which phenylphenol is within a range of 0.1 moles to 10.0 moles with respect to 1 mole of parabenzoquinone.

Among these phenolic resin exemplified, the phenolic resin (1) is preferable from the viewpoint of excellent heat resistance and flame retardancy of the cured product, and the phenolic resin (4) is preferable from the viewpoint of excellent heat resistance of the cured product.

In the phenolic resin of the present invention, the hydroxyl equivalent is preferably within a range of 50 g/eq to 150 g/eq from the viewpoint of excellent curing properties. In addition, the softening point is preferably within a range of 60° C. to 140° C.

The curable composition of the present invention contains the phenolic resin described above or a phenolic resin including the same, and a curing agent as essential components. As the curing agent, an epoxy resin is exemplified.

Specific examples of the epoxy resin used here include naphthalene skeleton-containing epoxy resins such as 1,6-diglycidyloxy naphthalene, 2,7-diglycidyloxy naphthalene, an α-naphthol novolak type epoxy resin, a β-naphthol novolak type epoxy resin, polyglycidyl ether of α-naphthol/β-naphthol co-condensed novolak, a naphthol aralkyl type epoxy resin, and 1,1-bis(2,7-diglycidyloxy-1-naphthyl)alkane; bisphenol type epoxy resins such as a bisphenol A type epoxy resin and a bisphenol F type epoxy resin; biphenyl type epoxy resins such as a biphenyl type epoxy resin and a tetramethyl biphenyl type epoxy resin; novolak type epoxy resins such as a phenol novolak type epoxy resin, a cresol novolak type epoxy resin, a bisphenol A novolak type epoxy resin, a bisphenol F novolak epoxy resin, an epoxidized product of a condensate of a phenol-based compound and an aromatic aldehyde having a phenolic hydroxyl group, and a biphenyl novolak type epoxy resin; triphenylmethane type epoxy resins; tetraphenyl ethane type epoxy resins; dicyclopentadiene-phenol addition reaction type epoxy resins; phenol aralkyl type epoxy resins; phosphorus atom-containing epoxy resins; and modified epoxy resins of the present invention.

In the case of using an epoxy resin as a curing agent, the blending proportion between the phenolic resin and the epoxy resin is preferably a proportion in which the equivalent ratio (phenolic hydroxyl group/epoxy group) of the phenolic hydroxyl group in the phenolic resin to the epoxy group in the epoxy resin is 1/0.5 to 1/1.5 since reactivity and heat resistance in terms of a cured product thereof are excellent at this proportion.

In addition, in the case of using an epoxy resin as a curing agent, in addition to the phenolic resin of the present invention, other curing agents for epoxy resin may be used in combination. As other curing agents for epoxy resin, various known curing agents such as an amine-based compound, an amide-based compound, an acid anhydride-based compound, and a phenol-based compound are exemplified. Specifically, examples of the amine-based compound include diaminodiphenyl methane, diethylenetriamine, triethylenetetramine, diaminodiphenyl sulfone, isophoronediamine, imidazole, $BF_3$-amine complex, and guanidine derivatives, examples of the amide-based compound include dicyandiamide and a polyamide resin synthesized from a linolenic acid dimer and ethylenediamine, examples of the acid anhydride-based compound include phthalic anhydride, trimellitic anhydride, pyromellitic anhydride, maleic anhydride, tetrahydrophthalic anhydride, methyl tetrahydrophthalic anhydride, methylnadic anhydride, hexahydrophthalic anhydride, and methylhexahydrophthalic anhydride, and examples of the phenol-based compound include polyvalent phenolic compounds such as a phenol novolak resin, a cresol novolak resin, an aromatic hydrocarbon formaldehyde resin-modified phenolic resin, a dicyclopentadiene phenol adduct type resin, a phenol aralkyl resin (Xylok resin), a naphthol aralkyl resin, a triphenylol methane resin, a tetraphenylol ethane resin, a naphthol novolak resin, a naphthol-phenol co-condensed novolak resin, a naphthol-cresol co-condensed novolak resin, a biphenyl-modified phenolic resin (polyvalent phenolic compound in which a phenolic nucleus is linked by a bismethylene group), a biphenyl-modified naphthol resin (polyvalent naphthol compound in which a phenolic nucleus is linked by a bismethylene group), an aminotriazine-modified phenolic resin (polyvalent phenolic compound in which a phenolic nucleus is linked by melamine, benzoguanamine, or the like), and an alkoxy group-containing aromatic ring-modified novolak resin (polyvalent phenolic compound in which a phenolic nucleus and an alkoxy group-containing aromatic ring is linked by a formaldehyde).

In the case of using other curing agents for epoxy resin, the blending proportion between the phenolic resin of the present invention and other curing agents for epoxy resin is not particularly limited as long as the characteristics of the phenolic resin of this application which exhibits excellent heat resistance and flame retardancy in terms of a cured product thereof are not impaired, and, for example, the phenolic resin of the present invention is preferably within a range of 5 parts by mass to 95 parts by mass in 100 parts by mass of the total mass of both.

In addition, in the case of using other curing agents for epoxy resin, the blending proportion with the epoxy resin is preferably a proportion in which the equivalent ratio (active hydrogen atom/epoxy group) between the total of active hydrogen atoms contained in the phenolic resin of the present invention and the epoxy group contained in the epoxy resin is 1/0.5 to 1/1.5 since reactivity and heat resistance of the cured product are excellent at this proportion.

In the curable composition of the present invention, a curing promoter can also be suitably used in combination as necessary. As the curing promoter, various curing promoters can be used, and examples thereof include phosphorus-based compounds, tertiary amines, imidazoles, organic acid metal salts, Lewis acids, and amine complex salts. In particular, in the case of using the curing promoter as semiconductor sealing material applications, 2-ethyl-4-methylimidazole as the imidazole compounds, triphenylphosphine as the phosphorus-based compounds, and 1,8-diazabicyclo-[5.4.0]-undecene (DBU) as the tertiary amines are preferable from the viewpoint of excellent curing properties, heat resistance, electrical characteristics, and moisture resistance reliability.

The curable composition of the present invention described above may further contain other additive components depending on the applications or the desired performance. Specifically, for the purposes of further improving flame retardancy, a non-halogen-based flame retardant which substantially does not contain a halogen atom may be blended.

Examples of the non-halogen-based flame retardant include a phosphorus-based flame retardant, a nitrogen-based flame retardant, a silicone-based flame retardant, an inorganic flame retardant, and an organometallic salt-based flame retardant. These may be used alone respectively, or plural types thereof may be used in combination.

As the phosphorus-based flame retardant, any one of an inorganic flame retardant and an organic flame retardant can be used, and examples of the inorganic flame retardant include inorganic nitrogen-containing phosphorus compounds such as ammonium phosphates including red phosphorus, monoammonium phosphate, diammonium phosphate, triammonium phosphate, and ammonium polyphosphate, and phosphoric amides.

The red phosphorus is preferably subjected to a surface treatment for the purpose of preventing hydrolysis or the like, and examples of the surface treatment method include (i) a method for coat-treating with an inorganic compound such as magnesium hydroxide, aluminum hydroxide, zinc hydroxide, titanium hydroxide, bismuth oxide, bismuth hydroxide, bismuth nitrate, or a mixture thereof, (ii) a method for coat-treating with an inorganic compound such as magnesium hydroxide, aluminum hydroxide, zinc hydroxide, or titanium hydroxide, and a mixture of a thermosetting resin such as a phenolic resin, and (iii) a method for doubly coat-treating the surface of a coated film of an inorganic compound such as magnesium hydroxide, aluminum hydroxide, zinc hydroxide, or titanium hydroxide with a thermosetting resin such as a phenolic resin.

Examples of the organic phosphorus-based compound include general-purpose organic phosphorus-based compounds such as a phosphoric acid ester compound, a phosphonic acid compound, a phosphinic acid compound, a phosphine oxide compound, a phosphorane compound, and an organic nitrogen-containing phosphorus compound, and cyclic organic phosphorus compounds such as 9,10-dihydro-9-oxa-10-phosphaphenanthrene-10-oxide, 10-(2,5-dihydroxyphenyl)-10H-9-oxa-10-phosphaphenanthrene-10-oxide, and 10-(2,7-dihydroxynaphthyl)-10H-9-oxa-10-phosphaphenanthrene-10-oxide, and derivatives obtained by reacting this with a compound such as an epoxy resin or a phenolic resin.

The blending amount thereof is suitably selected depending on the type of a phosphorus-based flame retardant, other components of a curable composition, and the desired degree of flame retardancy, and for example, in the case of using red phosphorus as a non-halogen-based flame retardant, the red phosphorus is preferably blended within a range of 0.1 parts by mass to 2.0 parts by mass, in the case of using an organic phosphorus compound, and the organic phosphorus compound is preferably blended within a range of 0.1 parts by mass to 10.0 parts by mass, and particularly preferably blended within a range of 0.5 parts by mass to 6.0 parts by mass, in 100 parts by mass of the curable composition obtained by blending all of the phenolic resin, a curing agent, and other additives, or a filler.

The blending amount thereof is suitably selected depending on the type of a phosphorus-based flame retardant, other components of a curable composition, and the desired degree of flame retardancy, and for example, in the case of using red phosphorus as a non-halogen-based flame retardant, the red phosphorus is preferably blended within a range of 0.1 parts by mass to 2.0 parts by mass, and in the case of using an organic phosphorus compound, the organic phosphorus compound is preferably blended within a range of 0.1 parts by mass to 10.0 parts by mass, and particularly preferably blended within a range of 0.5 parts by mass to 6.0 parts by mass, in 100 parts by mass of the curable composition.

In addition, in the case of using the phosphorus-based flame retardant, the phosphorus-based flame retardant may be used in combination with hydrotalcite, magnesium hydroxide, a boron compound, zirconium oxide, black dye, calcium carbonate, zeolite, zinc molybdate, or activated charcoal.

Examples of the nitrogen-based flame retardant include a triazine compound, a cyanuric acid compound, an isocyanuric acid compound, and phenothiazine, and the triazine compound, the cyanuric acid compound, or the isocyanuric acid compound is preferable.

Examples of the triazine compound include (i) aminotriazine sulfate compounds such as guanylic melamine sulfate, melem sulfate, and melam sulfate, (ii) co-condensates of a phenol-base compound such as phenol, cresol, xylenol, butylphenol, or nonylphenol, and melamines such as melamine, benzoguanamine, acetoguanamine, or formguanamine and formaldehyde, (iii) a mixture of the co-condensates of (ii) and phenolic resins such as a phenolformaldehyde condensate or the like, (iv) a product obtained by further modifying (ii) and (iii) with tung oil or isomerized linseed oil, or the like, in addition to melamine, acetoguanamine, benzoguanamine, melon, melam, succinoguanamine, ethylene dimelamine, melamine polyphosphate, and triguanamine.

Examples of the cyanuric acid compound can include cyanuric acid and melamine cyanurate.

The blending amount of the nitrogen-based flame retardant is suitably selected depending on the type of the nitrogen-based flame retardant, other components of a curable composition, and the desired degree of flame retardancy, and for example, the nitrogen-based flame retardant is preferably blended within a range of 0.05 parts by mass to 10 parts by mass, and particularly preferably blended within a range of 0.1 parts by mass to 5 parts by mass, in 100 parts by mass of the curable composition.

In addition, when using the nitrogen-based flame retardant, metal hydroxide or a molybdenum compound may be used in combination.

The silicone-based flame retardant can be used without any particular limitation as long as the silicone-based flame retardant is an organic compound containing a silicon atom, and examples thereof include silicone oil, silicone rubber, and silicone resins.

The blending amount of the silicone-based flame retardant is suitably selected depending on the type of the silicone-based flame retardant, other components of a curable composition, and the desired degree of flame retardancy, and for example, the silicone-based flame retardant is preferably blended within a range of 0.05 parts by mass to 20 parts by mass in 100 parts by mass of the curable composition. In addition, when using the silicone-based flame retardant, a molybdenum compound or alumina may be used in combination.

Examples of the inorganic flame retardant include metal hydroxides, metal oxides, metal carbonate compounds, metal powder, boron compounds, and low melting point glass.

Examples of the metal hydroxide can include aluminum hydroxide, magnesium hydroxide, dolomite, hydrotalcite, calcium hydroxide, barium hydroxide, and zirconium hydroxide.

Examples of the metal oxide can include zinc molybdate, molybdenum trioxide, zinc stannate, tin oxide, aluminum oxide, iron oxide, titanium oxide, manganese oxide, zirconium oxide, zinc oxide, molybdenum oxide, cobalt oxide, bismuth oxide, chromium oxide, nickel oxide, copper oxide, and tungsten oxide.

Examples of the metal carbonate compound can include zinc carbonate, magnesium carbonate, calcium carbonate, barium carbonate, basic magnesium carbonate, aluminum carbonate, iron carbonate, cobalt carbonate, and titanium carbonate.

Examples of the metal powder can include aluminum powder, iron powder, titanium powder, manganese powder, zinc powder, molybdenum powder, cobalt powder, bismuth powder, chromium powder, nickel powder, copper powder, tungsten powder, and tin powder.

Examples of the boron compound can include zinc borate, zinc metaborate, barium metaborate, boric acid, and borax.

Examples of the low melting point glass can include glass-like compounds such as a Ceepree (Bokusui Brown Co., Ltd.) glass, a hydrated glass $SiO_2$—$MgO$—$H_2O$, $PbO$—$B_2O_3$-based glass, a $ZnO$—$P_2O_5$—$MgO$-based glass, a $P_2O_5$—$B_2O_3$—$PbO$—$MgO$-based glass, a P—Sn—O—F-based glass, a $PbO$—$V_2O_5$—$TeO_2$-based glass, an $Al_2O_3$—$H_2O$-based glass, and lead borosilicate-based glass.

The blending amount of the inorganic flame retardant is suitably selected depending on the type of the inorganic flame retardant, other components of a curable composition, and the desired degree of flame retardancy, and for example, the inorganic flame retardant is preferably blended within a range of 0.5 parts by mass to 50 parts by mass, and particularly preferably blended within a range of 5 parts by mass to 30 parts by mass in 100 parts by mass of the curable composition.

Examples of the organometallic salt-based flame retardant include ferrocene, an acetylacetonate metal complex, an organometallic carbonyl compound, an organic cobalt salt compound, an organic sulfonic acid metal salt, and a compound obtained by an ionic bond or a coordination bond of a metal atom to an aromatic compound or a heterocyclic compound.

The blending amount of the organometallic salt-based flame retardant is suitably selected depending on the type of the organometallic salt-based flame retardant, other components of a curable composition, and the desired degree of flame retardancy, and for example, the silicone-based flame retardant is preferably blended within a range of 0.005 parts by mass to 10 parts by mass in 100 parts by mass of the curable composition.

In addition, various compounding agents such as a silane coupling agent, a release agent, a pigment, and an emulsifier can be added to the curable composition of the present invention, as necessary.

In the curable composition of the present invention, an inorganic filler can be blended, as necessary. Since the compound containing a phenolic hydroxyl group and the phenolic resin used in the present invention has low melt viscosity, it is possible to increase the blending amount of an inorganic filler, and such a curable composition can be suitably used in particularly semiconductor sealing material applications.

Examples of the inorganic filler include fused silica, crystalline silica, alumina, silicon nitride, and aluminum hydroxide. Among these, the fused silica is preferable since greater amount of the inorganic filler can be blended. The fused silica can be used in any one of a crushed shape or a spherical shape; however, in order to increase the blending amount of the fused silica and to suppress increase in melt viscosity of the curable composition, spherical silica is preferably mainly used. Furthermore, in order to increase the blending amount of the spherical silica, the particle size distribution of the spherical silica is preferably suitably adjusted. The filling ratio is preferably within a range of 0.5 parts by mass to 95 parts by mass in 100 parts by mass of the curable composition.

In addition, in the case of using the curable composition of the present invention in applications such as a conductive paste, it is possible to use a conductive filler such as silver powder or copper powder.

In the case of preparing the curable composition of the present invention in a varnish for a printed circuit board, an organic solvent is preferably blended. Examples of the organic solvent capable of being used here include methyl ethyl ketone, acetone, dimethylformamide, methyl isobutyl ketone, methoxypropanol, cyclohexanone, methyl cellosolve, ethyl diglycol acetate, and propylene glycol monomethyl ether acetate, and the selection and the suitable amount to be used can be suitably selected depending on the application, and, for example, in printed circuit board applications, polar solvents such as methyl ethyl ketone, acetone, and dimethylformamide having the boiling point of 160° C. or lower are preferable, and the solvents are preferably used in a proportion in which the non-volatile content becomes 40% by mass to 80% by mass. On the other hand, in adhesive film applications for build-up, as the organic solvent, for example, ketones such as acetone, methyl ethyl ketone, and cyclohexanone, acetic acid esters such as ethyl acetate, butyl acetate, cellosolve acetate, propylene glycol monomethyl ether acetate, and carbitol acetate, carbitols such as cellosolve and butyl carbitol, aromatic hydrocarbons such as toluene and xylene, dimethylformamide, dimethylacetamide, or N-methylpyrrolidone are preferably used, and the solvents are preferably used in a proportion in which the non-volatile content becomes 30% by mass to 60% by mass.

The curable composition of the present invention is obtained by uniformly mixing the respective components described above. The curable composition of the present invention obtained by blending the phenolic resin, a curing agent, and as necessary, a curing promoter can be easily cured by the same methods as methods known in the related art, whereby a cured product is formed. Examples of the cured product include molded cured products such as a laminate, a cast material, an adhesive layer, a coating film, and a film.

Since the phenolic resin of the present invention exhibit excellent heat resistance and flame retardancy in terms of a cured product thereof, the phenolic resin can be used in various electronic material applications. Among these, in particular, the phenolic resin can be suitably used in semiconductor sealing material applications.

The semiconductor sealing material can be prepared by a method in which a mixture of a phenol component including the phenolic resin of the present invention, a curing agent, and a filler is sufficiently mixed until it becomes uniform using an extruder, a kneader, or a roll. As the filler used here, the inorganic fillers described above are exemplified, and, as described above, the filler is preferably used within a range of 0.5 parts by mass to 95 parts by mass in 100 parts by mass of the curable composition. Among these, the filler is preferably used within a range of 70 parts by mass to 95 parts by mass, and particularly preferably used within a range of 80 parts by mass to 95 parts by mass, since flame retardancy, moisture resistance, and soldering crack resistance are improved, and a linear expansion coefficient can be reduced.

As a method for molding a semiconductor package using the obtained semiconductor sealing material, a method in which the semiconductor sealing material is formed using a casting, a transfer forming machine, or an injection molding machine, and the resultant product is heated for 2 hours to 10 hours under temperature conditions of 50° C. to 200° C. is exemplified, and by such a method, it is possible to obtain a semiconductor device which is a molded product.

In addition, in production of a printed circuit board using the phenolic resin of the present invention, a method which includes impregnating a reinforcement basic material with a vanish-like curable composition including the phenolic resin of the present invention, a curing agent, an organic solvent, and other additives, and superposing a copper foil on the resulting material, followed by heat-pressing is exemplified. Examples of the reinforcement basic material capable of being used here include paper, glass cloth, glass nonwoven fabric, aramid paper, aramid cloth, glass mat, and glass roving cloth. In describing the method in more detail, first, the vanish-like curable composition described above is heated at a heating temperature according to the solvent species used, preferably 50° C. to 170° C., whereby prepreg is obtained which is a cured product. The mass proportion between the curable composition and the reinforcement basic material used at this time is not particularly limited; however, typically, the prepreg is preferably prepared such that the resin content in the prepreg is 20% by mass to 60% by mass. Next, the prepreg obtained in the above manner is laminated by an ordinary method, then, copper foil is suitably superposed thereon, and the resultant product is heat-pressed at 170° C. to 250° C. for 10 minutes to 3 hours under a pressure of 1 MPa to 10 MPa, whereby a desired printed circuit board is obtained.

EXAMPLES

Hereinafter, the present invention will be more specifically described using examples and comparative examples, and "parts" and "%" below are based on mass unless otherwise specifically indicated. Moreover, a softening point, GPC, NMR, an MS spectrum were measured under the following conditions.

Softening point measurement method: based on JIS K7234.

GPC: the measurement conditions are as follows.
Measurement apparatus: "HLC-8220 GPC" manufactured by Tosoh Corporation
Column: guard column "HXL-L" manufactured by Tosoh Corporation+"TSK-GEL G2000HXL" manufactured by Tosoh Corporation+"TSK-GEL G2000HXL" manufactured by Tosoh Corporation+"TSK-GEL G3000HXL" manufactured by Tosoh Corporation+"TSK-GEL G4000HXL" manufactured by Tosoh Corporation
Detector: RI (differential refractometer)
Data processing: "GPC-8020 model II Version 4.10" manufactured by Tosoh Corporation
Measurement conditions: column temperature 40° C.
  eluent: tetrahydrofuran
  flow rate 1.0 ml/min
Standard: according to the measurement manual the "GPC-8020 model II Version 4.10", the following monodisperse polystyrene of which the molecular weight is known is used.
  (Polystyrene Used)
  "A-500" manufactured by Tosoh Corporation
  "A-1000" manufactured by Tosoh Corporation
  "A-2500" manufactured by Tosoh Corporation
  "A-5000" manufactured by Tosoh Corporation
  "F-1" manufactured by Tosoh Corporation
  "F-2" manufactured by Tosoh Corporation
  "F-4" manufactured by Tosoh Corporation
  "F-10" manufactured by Tosoh Corporation
  "F-20" manufactured by Tosoh Corporation
  "F-40" manufactured by Tosoh Corporation "F-80" manufactured by Tosoh Corporation
"F-128" manufactured by Tosoh Corporation
Sample: a solution (50 μl) obtained by filtering a tetrahydrofuran solution of 1.0% by mass in terms of the resin solid content through a microfilter.
$^{13}$C-NMR: the measurement conditions are as follows.
Apparatus: AL-400 manufactured by JEOL Ltd.
Measurement mode: SGNNE (1H complete decoupling method of NOE elimination)
Solvent: dimethylsulfoxide
Pulse angle: 450 pulse
Sample concentration: 30% by weight
Cumulated number: 10,000 times
MS: double focusing mass spectrometer "AX505H (FD505H)" manufactured by JEOL Ltd.

Example 1

Preparation of Phenolic Resin (1)

282 parts by mass (3 moles) of phenol and 3 parts by mass of para-toluenesulfonic acid were put into a flask equipped with a thermometer, a dropping funnel, a cooling tube, a fractionating column, and a stirrer, and the resultant product was heated from room temperature to 80° C. with stirring. After the temperature reached 80° C., 162 parts by mass (1.5 moles) of parabenzoquinone was added thereto for a period of 1 hour, then, the temperature was raised to 130° C., and stirring was performed for 1 hour to react. After the reaction ended, the resultant product was dried under reduced pressure, whereby 250 parts by mass of a phenolic resin (1) was obtained. A GPC chart of the obtained phenolic resin is shown in FIG. 1, a 13C-NMR spectrum of the obtained phenolic resin is shown in FIG. 2, and an MS spectrum of the obtained phenolic resin is shown in FIG. 3. The hydroxyl equivalent of the phenolic resin (1) was 88 g/eq, and the softening point thereof was 95° C. A peak of 202 corresponding to the binuclear compound (X), a peak of 294 corresponding to the trinuclear compound (Y), and a peak of 386 corresponding to the tetranuclear compound (Z) were detected from the MS spectrum. The content of the component corresponding to the binuclear compound (X) was 37.3%, the content of the component corresponding to the trinuclear compound (Y) was 30.7%, and the content of the component corresponding to the tetranuclear compound (Z) was 10.3% in the phenolic resin, calculated from the GPC chart.

Example 2

Preparation of Phenolic Resin (2)

649 parts by mass (6.0 moles) of ortho-cresol and 3 parts by mass of para-toluenesulfonic acid were put into a flask equipped with a thermometer, a dropping funnel, a cooling tube, a fractionating column, and a stirrer, and the resultant product was heated from room temperature to 80° C. with stirring. After the temperature reached 80° C., 162 parts by mass (1.5 moles) of parabenzoquinone was added thereto for a period of 1 hour, then, the temperature was raised to 130° C., and stirring was performed for 1 hour to react. After the reaction ended, the resultant product was dried under reduced pressure, whereby 260 parts by mass of a phenolic resin (2) was obtained. The obtained GPC chart of the phenolic resin (2) is shown in FIG. 4. The hydroxyl equivalent of the phenolic resin (2) was 97 g/eq, and the softening point thereof was 88° C. The content of the component corresponding to the binuclear compound (X) was 25.8%, the content of the component corresponding to the trinuclear compound (Y) was 51.7%, and the content of the component corresponding to the tetranuclear compound (Z) was 10.0% in the phenolic resin, calculated from the GPC chart.

Example 3

Preparation of Phenolic Resin (3)

165 parts by mass (1.5 moles) of resorcin and 162 parts by mass (1.5 moles) of parabenzoquinone were put into a flask equipped with a thermometer, a dropping funnel, a cooling tube, a fractionating column, and a stirrer, and the resultant product was heated from room temperature to 120° C. with stirring. After the temperature reached 120° C., stirring was performed for 2 hours. After the reaction ended, the temperature was heated to 180° C., and the resultant product was dried under reduced pressure, whereby 280 parts by mass of a phenolic resin (3) was obtained. A GPC chart of the obtained phenolic resin (3) is shown in FIG. 5, a 13C-NMR spectrum of the obtained phenolic resin (3) is shown in FIG. 6, and an MS spectrum of the obtained phenolic resin (3) is shown in FIG. 7. The hydroxyl equivalent of the phenolic resin (3) was 60 g/eq, and the softening point thereof was 98° C. Peaks of 202 and 218 corresponding to the binuclear compound (X), peaks of 310 and 326 corresponding to the trinuclear compound (Y), and peaks of 418 and 434 corresponding to the tetranuclear compound (Z) were detected from the MS spectrum. The content of the component corresponding to the binuclear compound (X) was 20.0%, the content of the component corresponding to the trinuclear compound (Y) was 20.8%, and the content of the component corresponding to the tetranuclear compound (Z) was 13.0% in the phenolic resin, calculated from the GPC chart.

Example 4

Preparation of Phenolic Resin (4)

248 parts by mass (2.25 moles) of resorcin and 162 parts by mass (1.5 moles) of parabenzoquinone were put into a flask equipped with a thermometer, a dropping funnel, a cooling tube, a fractionating column, and a stirrer, and the resultant product was heated from room temperature to 120° C. with stirring. After the temperature reached 120° C., stirring was performed for 2 hours. After the reaction ended, the temperature was heated to 180° C., and the resultant product was dried under reduced pressure, whereby 290 parts by mass of a phenolic resin (4) was obtained. The obtained GPC chart of the phenolic resin (4) is shown in FIG. 8. The hydroxyl equivalent of the phenolic resin (4) was 60 g/eq, and the softening point thereof was 79° C. The content of the component corresponding to the binuclear compound (X) was 16.3%, the content of the component corresponding to the trinuclear compound (Y) was 18.7%, and the content of the component corresponding to the tetranuclear compound (Z) was 10.5% in the phenolic resin, calculated from the GPC chart.

Examples 5 to 8 and Comparative Example 1

Evaluation test of heat resistance and flame retardancy was performed on the phenolic resins (1) to (4) obtained above, and aphenolic resin (1') for comparison [triphenylmethane type phenolic resin ("MEH-7500" manufactured by Meiwa Plastic Industries, Ltd., hydroxyl equivalent of 98 g/eq)] in the following manner.

<Evaluation of Heat Resistance>

1) Production of Evaluation Sample

Any one of the phenolic resins (1) to (4), and (1'), a naphthalene type epoxy resin ("EXA-4750" manufactured by DIC Corporation, epoxy equivalent of 188 g/eq) as a curing agent, and triphenylphosphine (hereinafter, abbreviated as "TPP") as a curing promoter were blended according to the composition ratios shown in the following Table 2, whereby curable compositions were obtained. Each of these was poured into a mold of 11 cm×9 cm×2.4 mm and molded at a temperature of 150° C. for 10 minutes using a press. After the molded product was taken out from the mold, the molded product was cured at a temperature of 175° C. for 5 hours, whereby an evaluation sample was obtained.

2) Measurement of Glass Transition Temperature

A measurement of the temperature at which the change in elastic modulus becomes maximum (at which tan δ change ratio is the greatest) was performed on the evaluation sample using a viscoelasticity measuring apparatus (DMA: solid viscoelasticity measuring apparatus RSAII manufactured by Rheometric Scientific Inc., rectangular tension method; frequency of 1 Hz, temperature raising rate of 3° C./min), and this is evaluated as the glass transition temperature. The results are shown in Table 1.

TABLE 1

|  | Example 5 | Example 6 | Example 7 | Example 8 | Comparative Example 1 |
|---|---|---|---|---|---|
| Phenolic resin (1) | 31.9 | | | | |
| Phenolic resin (2) | | 34.0 | | | |
| Phenolic resin (3) | | | 24.2 | | |
| Phenolic resin (4) | | | | 24.2 | |
| MEH-7500 | | | | | 34.3 |
| EXA-4750 | 68.1 | 66.0 | 75.8 | 75.8 | 65.7 |
| TPP | 1.0 | 1.0 | 1.0 | 1.0 | 1.0 |
| Heat resistance (° C.) | 232 | 230 | 252 | 232 | 215 |

<Evaluation of Flame Retardancy>

1) Production of Evaluation Sample

Any one of the phenolic resins (1) to (4), and (1'), a naphthalene type epoxy resin ("EXA-4750" manufactured by DIC Corporation, epoxy equivalent of 188 g/eq) as a curing agent, triphenylphosphine (hereinafter, abbreviated as "TPP") as a curing promoter, spherical silica ("FB-5604" manufactured by Denki Kagaku Kogyo Kabushiki Kaisha) as an inorganic filler, a coupling agent ("KBM-403" manufactured by Shin-Etsu Chemical Co., Ltd.) as a silane coupling agent, carnauba wax ("PEARL WAX No. 1-P" manufactured by Cerarica Noda Co., Ltd.), and carbon black were blended according to the composition ratios shown in the following Table 3, and the resultant products were melted and kneaded at a temperature of 85° C. for 5 minutes using a two roll, whereby curable compositions were obtained. Using the obtained curable composition, a sample having a size of 12.7 mm in width, 127 mm in length and 1.6 mm in thickness was molded at a temperature of 175° C. for 90 seconds using a transfer molding machine, and the sample was cured at a temperature of 175° C. for 5 hours, whereby an evaluation sample was obtained.

2) Evaluation of Flame Retardancy

A combustion test was carried out in conformity with a UL-94 test method using the five samples for evaluation having a thickness of 1.6 mm obtained before. The results are shown in Table 2.

Flame Retardant Test Class
*1: maximum combustion time (seconds) in a single flame contact
*2: total combustion time (seconds) of five test pieces

TABLE 2

|  | Example 5 | Example 6 | Example 7 | Example 8 | Comparative Example 1 |
|---|---|---|---|---|---|
| Phenolic resin (1) | 37.6 | | | | |
| Phenolic resin (2) | | 40.2 | | | |
| Phenolic resin (3) | | | 28.5 | | |
| Phenolic resin (4) | | | | 28.5 | |
| MEH-7500 | | | | | 40.4 |
| EXA-4750 | 80.4 | 77.8 | 89.5 | 89.5 | 77.6 |
| TPP | 2 | 2 | 2 | 2 | 2 |
| Spherical silica | 870 | 870 | 870 | 870 | 870 |
| Coupling agent | 4 | 4 | 4 | 4 | 4 |
| Carnauba wax | 4 | 4 | 4 | 4 | 4 |
| Carbon black | 2 | 2 | 2 | 2 | 2 |
| Flame retardant test class | V-0 | V-0 | V-0 | V-0 | Combustion |
| *1 | 6 | 8 | 9 | 8 | 38 |
| *2 | 40 | 47 | 48 | 46 | 266 |

The invention claimed is:

1. A curable composition comprising, as essential components:
   a phenolic resin; and a curing agent,
   wherein the phenolic resin comprises, as essential components:
   a binuclear compound (X) represented by the following Structural Formula (I); and
   a trinuclear compound (Y) represented by the following Structural Formula (II),

[Chem. 1]

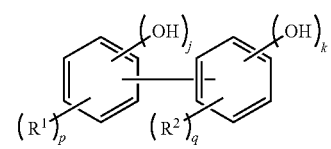

(I)

wherein each of $R^1$ and $R^2$ is an alkyl group having 1 to 4 carbon atoms, each of p and q is 0, 1 or 2, in a case where p or q is 2, two $R^1$'s or $R^2$'s may be the same as or different from each other, each of j and k is 1 or 2, and at least one of j and k is 2;

[Chem. 2]

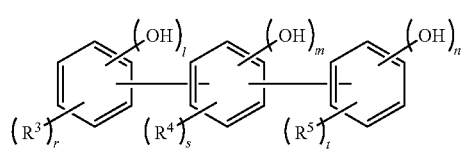

(II)

wherein each of $R^3$, $R^4$, and $R^5$ is an alkyl group having 1 to 4 carbon atoms, each of r, s and t is 0, 1 or 2, in a case where r, s or t is 2, two $R^3$'s, $R^4$'s or $R^5$'s may be the same as or different from each other, each of l, m and n is 1 or 2, and at least one of l, m and n is;
and wherein in the phenolic resin, the content of the binuclear compound (X) is within a range of 2% to 50% in area ratio in a GPC measurement, and the content of the trinuclear compound (Y) is within a range of 10% to 95% in area ratio in a GPC measurement.

2. A cured product obtained by a curing reaction of the curable composition according to claim 1.

3. A semiconductor sealing material, comprising:
the curable composition according to claim 1; and
an inorganic filler.

4. A printed circuit board obtained by impregnating a reinforcement basic material with a resin composition obtained by blending the curable composition according to claim 1 with an organic solvent, and superposing a copper foil on the resulting material, followed by heat-pressing.

5. The curable composition according to claim 1,
wherein the binuclear compound (X) represented by the following Structural Formula (I); and the trinuclear compound (Y) represented by the following Structural Formula (II-1) or (II-2),

[Chem. 3]

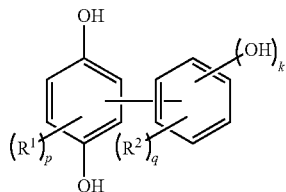

(I)

wherein each of $R^1$ and $R^2$ is any one of an alkyl group having 1 to 4 carbon atoms, each of p and q is 0, 1 or 2, in a case where p or q is 2, two $R^1$'s or $R^2$'s may be the same as or different from each other, k is 1 or 2;

[Chem. 4]

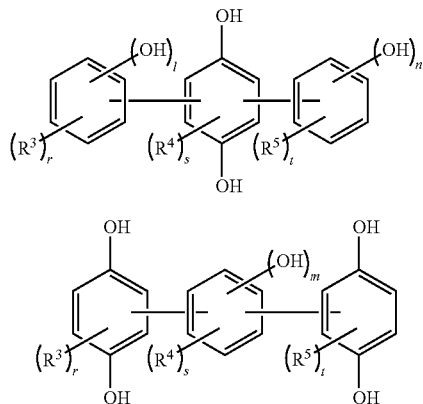

wherein each of $R^3$, $R^4$, and $R^5$ is any one of an alkyl group having 1 to 4 carbon atoms, each of r, s and t is 0, 1 or 2, in a case where r, s or t is 2, two $R^3$'s, $R^4$'s or $R^5$'s may be the same as or different from each other, each of l, m and n is 1 or 2.

6. The curable composition according to claim 1,
wherein the binuclear compound (X) represented by the following Structural Formula (I); and the trinuclear compound (Y) represented by the following Structural Formula (II-1) or (II-2),

[Chem. 5]

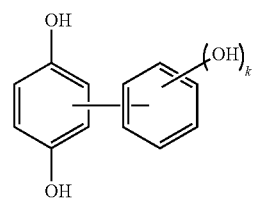

(I)

wherein k is 1 or 2;

[Chem. 6]

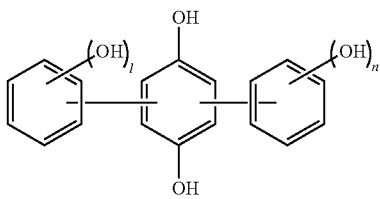

(II-1)

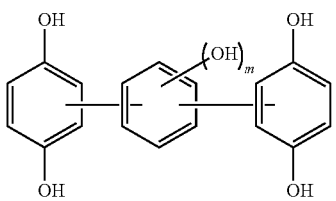

(II-2)

wherein each of l, m and n is 1 or 2.

* * * * *